United States Patent [19]
Dunlap et al.

[11] Patent Number: 5,855,566
[45] Date of Patent: Jan. 5, 1999

[54] TROCAR ASSEMBLY

[75] Inventors: David A. Dunlap, Portage; Douglas J. Medema, Plainwell; Hugh Melling, Richland; Jeffrey W. Zerfas, Grandville, all of Mich.

[73] Assignee: UroHealth, Inc. (California), Newport Beach, Calif.

[21] Appl. No.: 457,973

[22] Filed: Jun. 1, 1995

Related U.S. Application Data

[62] Division of Ser. No. 189,318, Jan. 31, 1994, Pat. No. 5,538,509.

[51] Int. Cl.⁶ .................................................. A61B 17/00
[52] U.S. Cl. ............................................. 604/164; 604/256
[58] Field of Search .................................. 604/158, 164, 604/167, 256, 165, 171, 174, 175, 178, 264, 272

[56] References Cited

U.S. PATENT DOCUMENTS

| | | | |
|---|---|---|---|
| D. 320,857 | 10/1991 | Tompkins et al. | D24/146 |
| D. 338,270 | 8/1993 | Stephens et al. | D24/140 |
| 1,147,508 | 7/1915 | Kells | 604/272 |
| 1,213,001 | 1/1917 | Philips . | |
| 1,835,287 | 12/1931 | Donovan . | |
| 2,097,039 | 10/1937 | Peterson | 128/347 |
| 2,496,111 | 1/1950 | Turkel | 128/2 |
| 2,525,329 | 10/1950 | Wyzenbeek | 128/347 |
| 2,541,542 | 2/1951 | Perez et al. | 128/2 |
| 2,623,521 | 12/1952 | Shaw | 128/221 |
| 3,007,471 | 11/1961 | McClure, Jr. | 128/2 |
| 3,039,468 | 6/1962 | Price | 128/347 |
| 3,090,384 | 5/1963 | Baldwin et al. | 128/221 |
| 3,241,554 | 3/1966 | Coanda | 128/350 |
| 3,253,594 | 5/1966 | Matthews et al. | 128/348 |
| 3,459,175 | 8/1969 | Miller | 128/2 |
| 3,459,189 | 8/1969 | Alley et al. | 128/347 |
| 3,540,447 | 11/1970 | Howe | 128/221 |
| 3,545,443 | 12/1970 | Ansari | 128/347 |
| 3,565,074 | 2/1971 | Foti et al. | 128/214.4 |
| 3,613,684 | 10/1971 | Sheridan | 128/347 |
| 3,721,229 | 3/1973 | Panzer | 128/2 A |

(List continued on next page.)

FOREIGN PATENT DOCUMENTS

| | | |
|---|---|---|
| 0413493A2 | 2/1991 | European Pat. Off. . |
| 461568 | 12/1991 | European Pat. Off. ............... 604/158 |
| 3713829A | 10/1988 | Germany . |
| 475215 | 2/1951 | Italy . |
| 2161709 | 1/1986 | United Kingdom . |

OTHER PUBLICATIONS

"Surgical Trocars with Sureseal™ Valve," Brochure of Applied Medical Resources, Copyright 1992, 2 pages.

"Blunt–Tip Trocar," Brochure of Origin Medsystems, Inc., Copyright 1992, 2 pages.

"Thoracic Trocar," Brochure of Origin Medsystems, Inc., Copyright 1992, 2 pages.

"Bold by Design," Endopath TriStar Disposable Surgical Trocar, by Ethicon Endosurgery, Copyright 1992, 1 page.

"Hunt/Reich Secondary Cannula Provides Major Cost Savings," Brochure of Apple Medical Corp., 2 pages.

(List continued on next page.)

Primary Examiner—Sam Rimell

[57] ABSTRACT

A trocar for use in surgical procedures including a cannula for maintaining a sealed working channel in a body wall and an obturator which creates the working channel through the body wall while protecting patients and medical personnel from harm is disclosed. A cannula converter which can be employed with the trocar to enable a surgeon to use surgical instruments having a smaller outer diameter than the inner diameter of the cannula without deflating a body cavity is further disclosed. A site stabilizer which can be used with the trocar to prevent the cannula from being inadvertently withdrawn from the body cavity during a surgical procedure is also disclosed.

7 Claims, 14 Drawing Sheets

U.S. PATENT DOCUMENTS

| | | | |
|---|---|---|---|
| 3,750,667 | 8/1973 | Pshenichny et al. | 128/215 |
| 3,789,852 | 2/1974 | Kim et al. | 128/347 |
| 3,817,250 | 6/1974 | Weiss et al. | 128/305 |
| 3,817,251 | 6/1974 | Hasson | 128/348 |
| 3,860,006 | 1/1975 | Patel | 128/347 |
| 3,893,446 | 7/1975 | Miller | 128/2 A |
| 3,895,632 | 7/1975 | Ploweicki | 128/214.4 |
| 3,948,270 | 4/1976 | Hasson | 128/348 |
| 3,993,079 | 11/1976 | Henriques de Gatztanondo | 128/347 |
| 3,994,287 | 11/1976 | Turp et al. | 128/6 |
| 4,014,080 | 3/1977 | Froning | 128/347 |
| 4,058,121 | 11/1977 | Choski et al. | 128/221 |
| 4,177,814 | 12/1979 | Knepshield et al. | 128/348 |
| 4,180,068 | 12/1979 | Jacobsen et al. | 128/214 R |
| 4,186,750 | 2/1980 | Patel | 128/748 |
| 4,215,699 | 8/1980 | Patel | 128/748 |
| 4,230,123 | 10/1980 | Hawkins, Jr. | 128/658 |
| 4,254,762 | 3/1981 | Yoon | 128/4 |
| 4,299,230 | 11/1981 | Kubota | 128/630 |
| 4,325,370 | 4/1982 | Young | 128/245 |
| 4,345,589 | 8/1982 | Hiltebrandt | 128/4 |
| 4,414,974 | 11/1983 | Dotson et al. | 128/305 |
| 4,419,094 | 12/1983 | Patel | 604/93 |
| 4,447,236 | 5/1984 | Quinn | 604/169 |
| 4,491,132 | 1/1985 | Aikins | 128/305 |
| 4,496,345 | 1/1985 | Hasson | 604/103 |
| 4,523,379 | 6/1985 | Osterhout et al. | 30/151 |
| 4,535,773 | 8/1985 | Yoon | 604/51 |
| 4,556,059 | 12/1985 | Adamson, Jr. | 128/305.3 |
| 4,601,710 | 7/1986 | Moll | 604/165 |
| 4,627,838 | 12/1986 | Cross et al. | 604/105 |
| 4,645,492 | 2/1987 | Weeks | 604/174 |
| 4,650,473 | 3/1987 | Bartholomew et al. | 604/174 |
| 4,654,030 | 3/1987 | Moll et al. | 604/165 |
| 4,668,222 | 5/1987 | Poirier | 604/175 |
| 4,670,008 | 6/1987 | Von Albertini | 604/165 |
| 4,755,173 | 7/1988 | Konopka et al. | 604/51 |
| 4,772,261 | 9/1988 | Von Hoff et al. | 604/51 |
| 4,808,168 | 2/1989 | Warring | 604/165 |
| 4,894,052 | 1/1990 | Crawford | 604/63 |
| 4,902,280 | 2/1990 | Lander | 604/165 |
| 4,931,042 | 6/1990 | Holmes et al. | 604/164 |
| 4,943,280 | 7/1990 | Lander | 604/169 |
| 4,969,870 | 11/1990 | Kramer et al. | 604/51 |
| 5,002,557 | 3/1991 | Hasson | 606/191 |
| 5,009,643 | 4/1991 | Reich et al. | 606/165 |
| 5,030,206 | 7/1991 | Lander | 604/164 |
| 5,053,016 | 10/1991 | Lander | 604/169 |
| 5,057,085 | 10/1991 | Kopans | 604/173 |
| 5,066,288 | 11/1991 | Deneiga et al. | 604/274 |
| 5,085,648 | 2/1992 | Purdy et al. | 604/198 |
| 5,104,382 | 4/1992 | Brinkerhoff et al. | 604/165 |
| 5,104,383 | 4/1992 | Shichman | 604/167 |
| 5,114,407 | 5/1992 | Burbank | 604/164 |
| 5,116,353 | 5/1992 | Green | 606/184 |
| 5,127,909 | 7/1992 | Shichman | 604/165 |
| 5,129,885 | 7/1992 | Green et al. | 604/164 |
| 5,139,487 | 8/1992 | Baber | 604/165 |
| 5,141,517 | 8/1992 | Shutt | 606/167 |
| 5,143,082 | 9/1992 | Kindberg et al. | 128/749 |
| 5,144,942 | 9/1992 | Decarie et al. | 128/4 |
| 5,147,316 | 9/1992 | Castillenti | 604/164 |
| 5,152,754 | 10/1992 | Plyley et al. | 604/164 |
| 5,158,552 | 10/1992 | Borgia et al. | 604/165 |
| 5,217,441 | 6/1993 | Schichman | 604/164 X |
| 5,226,890 | 7/1993 | Ianniruberto et al. | 604/174 X |
| 5,234,455 | 8/1993 | Mulhollan | 606/191 |
| 5,256,149 | 10/1993 | Banik et al. | 604/164 |
| 5,257,973 | 11/1993 | Villasuso | 604/49 |
| 5,257,975 | 11/1993 | Foshee | 604/105 |
| 5,284,474 | 2/1994 | Adair | 604/164 |
| 5,287,852 | 2/1994 | Arkinstall | 128/207.14 |
| 5,318,585 | 6/1994 | Guy et al. | 604/164 X |
| 5,336,206 | 8/1994 | Schichman | 604/164 X |
| 5,370,625 | 12/1994 | Schichman | 604/174 |
| 5,395,342 | 3/1995 | Yoon | 604/164 X |
| 5,431,151 | 7/1995 | Riek et al. | 604/164 X |
| 5,437,646 | 8/1995 | Hunt et al. | 604/256 X |
| 5,441,487 | 8/1995 | Vedder | 604/256 X |

OTHER PUBLICATIONS

"Advanced Laparoscopy with Auto Suture," Brochure of Auto Suture International, Inc., Copyright 1992, 2 pages.

"Laparoscopic Products Catalogue," Dexide, Inc., Copyright 1991, 4 pages.

"Entree™," Brochure of Core Dynamics, Inc., Copyright 1992, 2 pages.

"Trocan™," Brochure of Cabot Medical, Copyright Mar. 1991, 2 pages.

"The Source of Laparoscopic Innovation Origin," Brochure of Origin Medsystems, Inc., Copyright 1992, 4 pages.

"Lock into the Cutting Edge of Laparoscopy," Brochure of Dexide, Inc., Copyright 1992, 6 pages.

Distributor Price List of Ethicon Endo–Surgery, dated Feb. 24, 1992, Front Cover, pp. 7–11 and 38–39.

"Innovations in Endosurgery," The Endopath Disposable Blunt Tip Trocar for Open Laparoscopy, Brochure of Ethicon, Inc., Copyright 1991, 1 page.

"Endopath," Trokare Veress–Naeln, Brochure of Ethicon GMBH & Co. Inc., Copyright 1992, 4 pages.

"Auto Suture Disposable Laparoscopic System," Brochure of Auto Suture, United States Surgical Corporation and Century Medical, Inc., 4 pages.

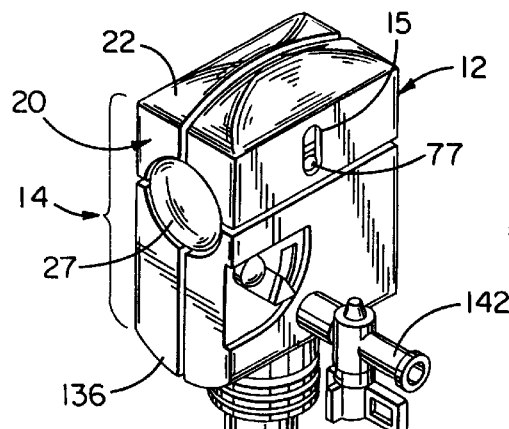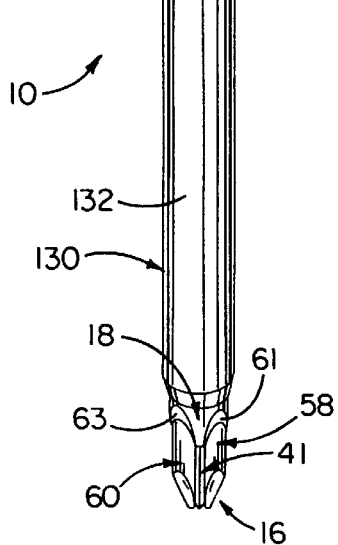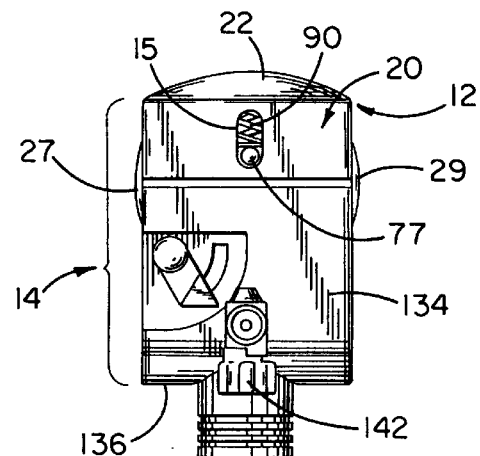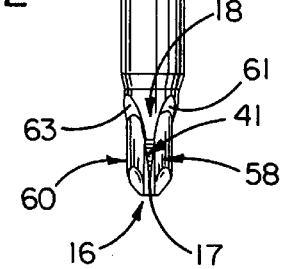
FIG. 1
FIG. 2

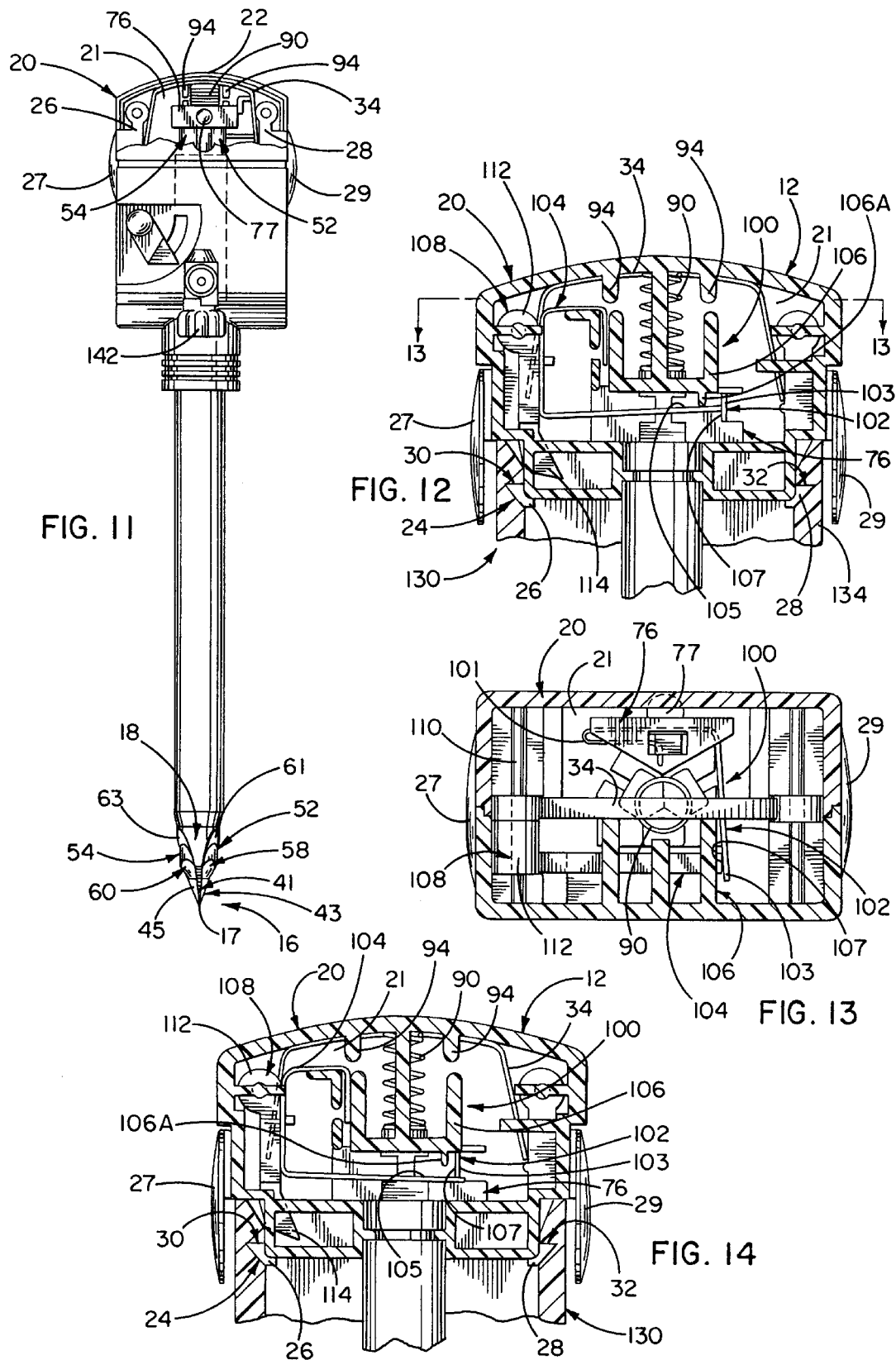

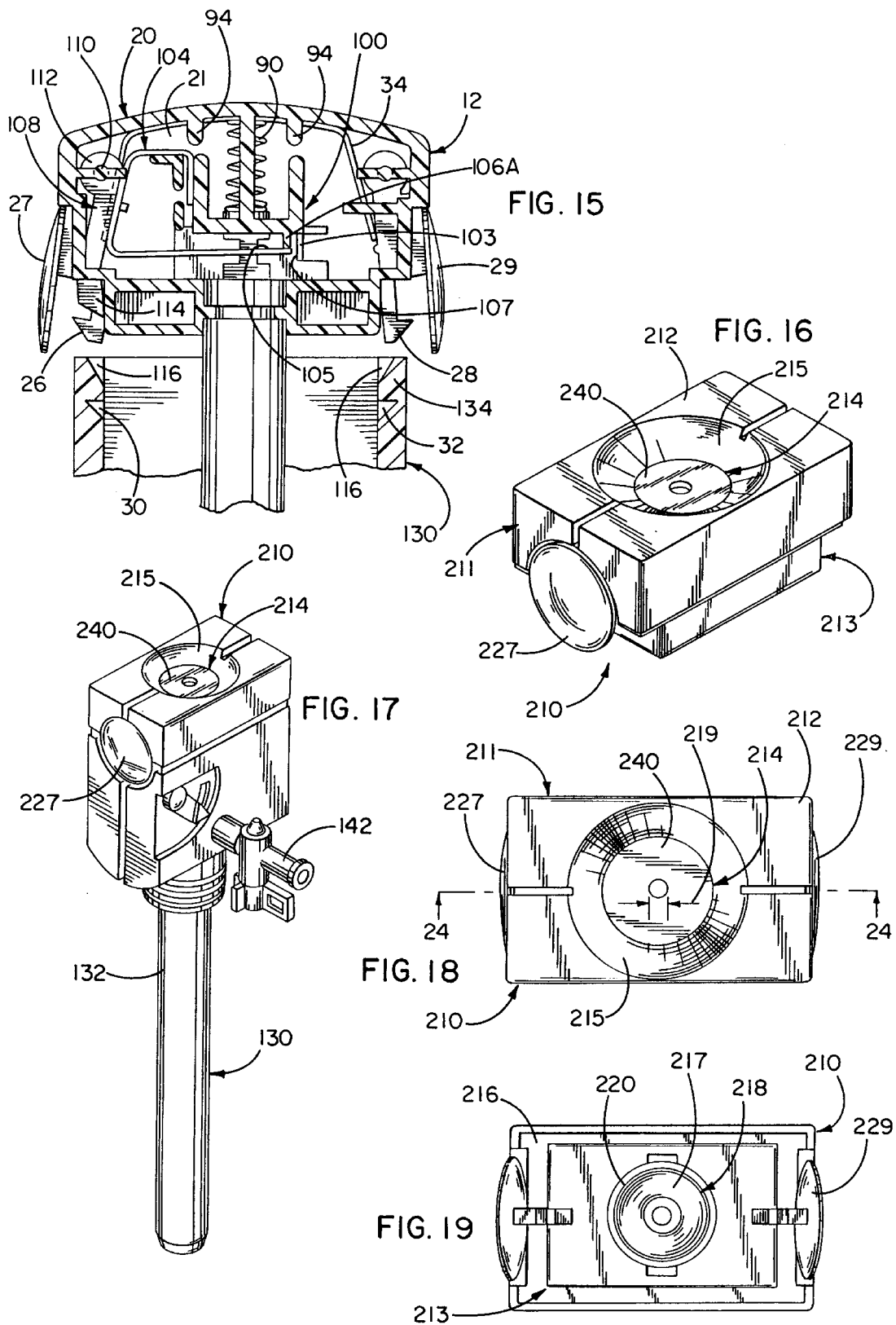

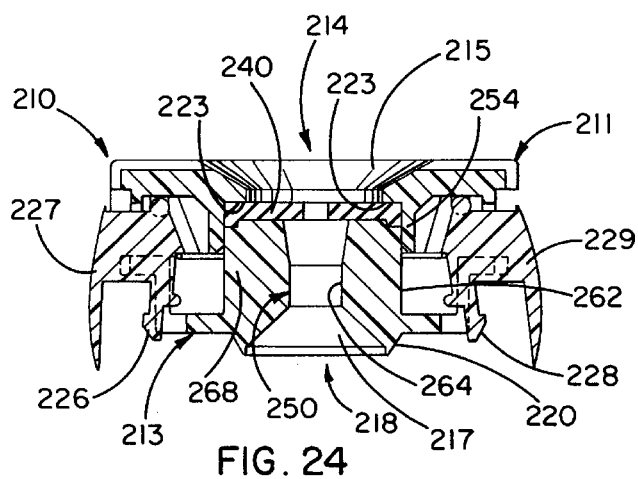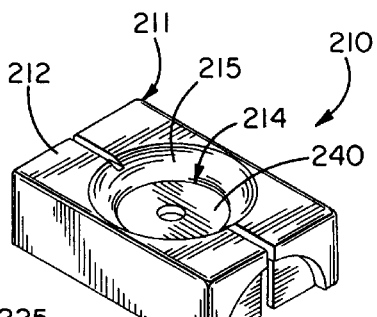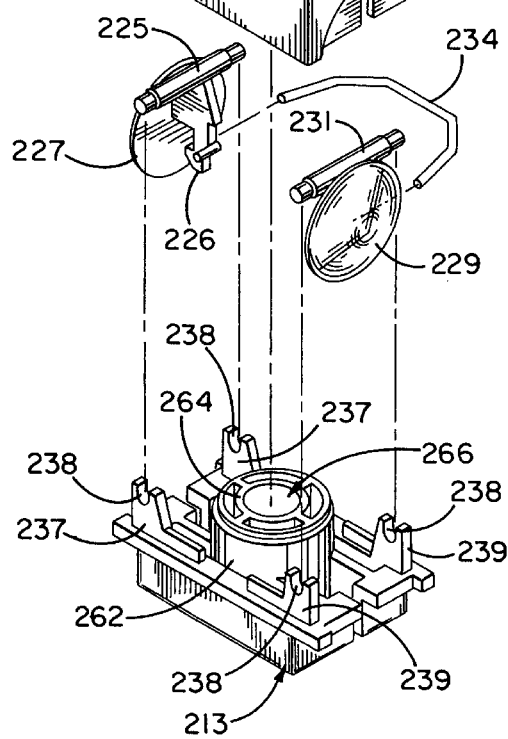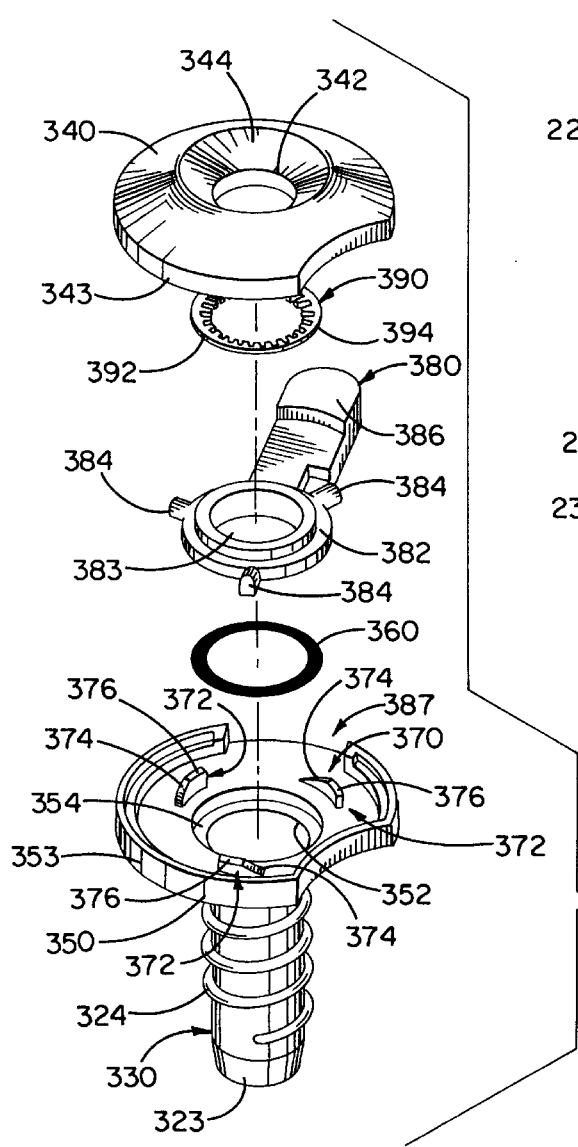

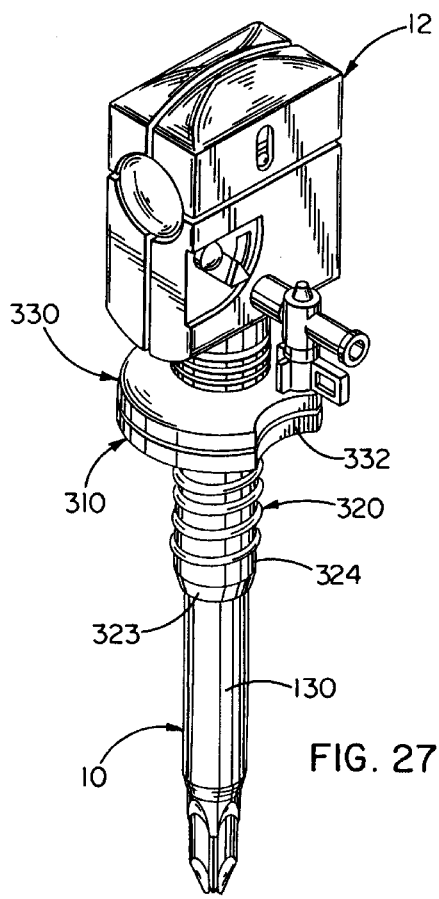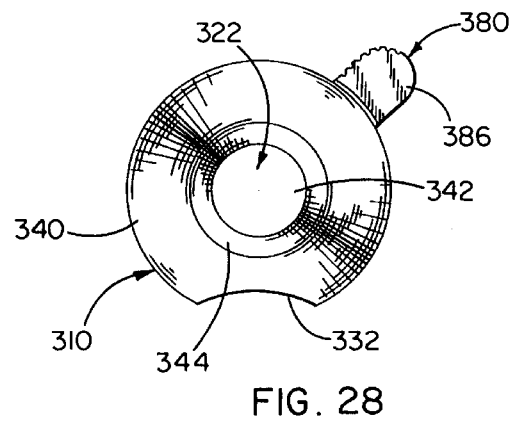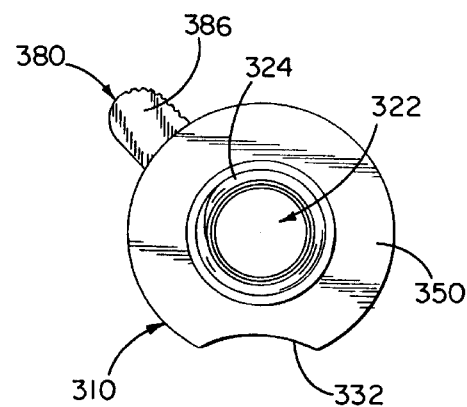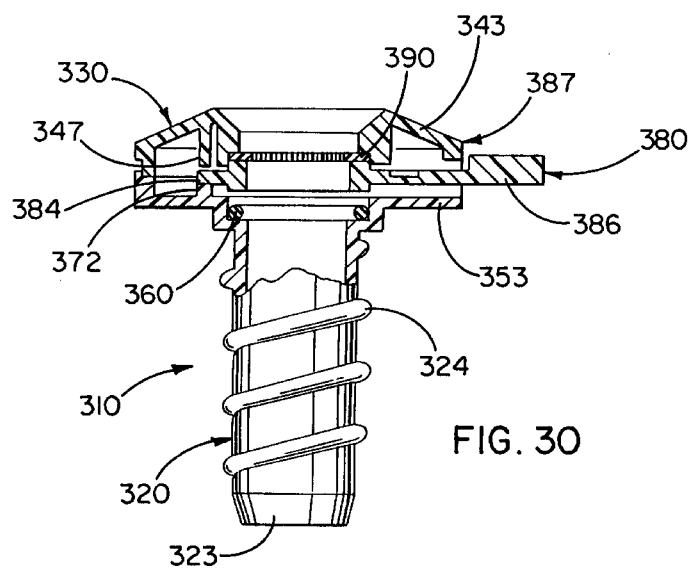
FIG. 27
FIG. 28
FIG. 29
FIG. 30

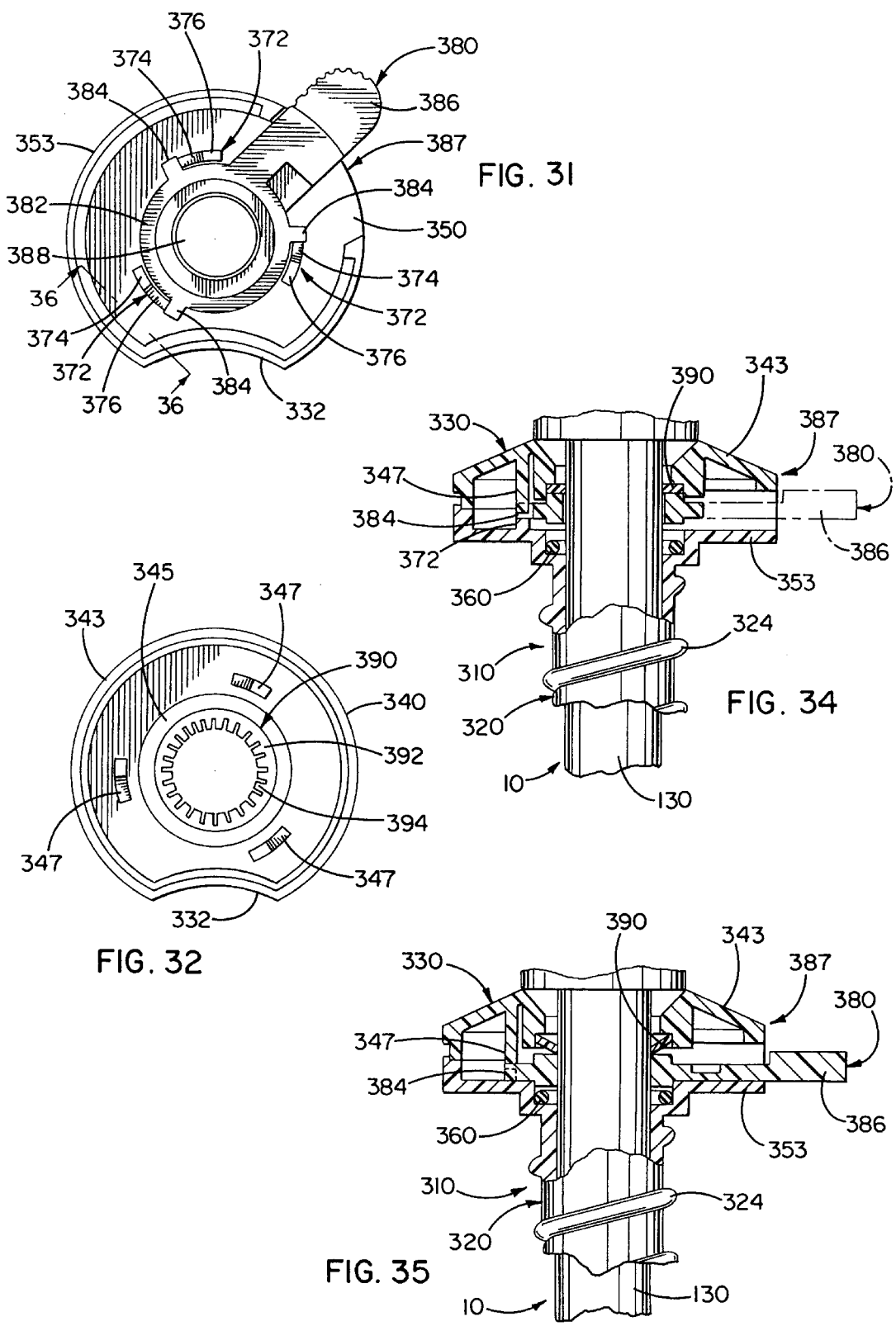

TROCAR ASSEMBLY

This application is a division of U.S. application Ser. No. 08/189,318, filed Jan. 31, 1994, now U.S. Pat. No. 5,538,509.

FIELD OF THE INVENTION

The invention relates generally to surgical instruments and more particularly to trocars for use in surgical procedures.

BACKGROUND OF THE INVENTION

Medical science has long sought ways to minimize the dangers and trauma inherent in invasive surgical procedures. To this end, surgical techniques and instruments have been developed which, among other things, reduce the size of the incisions required to perform various surgical procedures. These techniques and instruments have been remarkably successful. Indeed, surgical procedures which only a few years ago would require an incision six or seven inches in length are today being performed through incisions which are less than one inch in length.

Trocars are one type of surgical instrument which have significantly contributed to these advances. In general, trocars are sharp, pointed surgical instruments which can be used to create and maintain small, hole-like incisions in a body cavity. Surgical instruments, including miniaturized optical devices, can be inserted through these small incisions and manipulated to perform surgical procedures within the body cavity without ever exposing the patient's internal organs or structures to the outside environment. Thus, by enabling the creation and maintenance of small working holes within a patient's body wall, conventional trocars have greatly contributed to the reduction in size of the incisions required to perform surgical procedures and reduced the related complications.

Conventional trocars generally include an obturator and a cannula. An obturator is a sharp, nail-like structure for penetrating a body wall to create a working channel into the body cavity. A cannula is a tube-like structure which can be inserted into the incision made by the obturator to maintain the working channel even after the obturator is removed. In the typical scenario, the obturator and cannula are assembled into a single unit (i.e., by inserting the obturator into the cannula) and then used to puncture the body wall. The obturator can then be carefully withdrawn from the cannula without removing the cannula from the body wall. Surgical instruments can be inserted through this cannula to perform an entire surgical procedure within the body cavity as mentioned above.

While conventional trocars plainly have many benefits, they also present significant hazards to both patients and medical personnel. For example, a patient is placed at risk of serious injury by the manner in which the trocar is employed. Specifically, in order to insert a trocar into a patient, a physician must overcome the resistance of the patient's body wall by exerting a significant amount of pressure on the trocar. When the obturator tip passes beyond the body wall the resistance suddenly reduces significantly. Thus, unless the physician immediately stops applying force, the trocar can move rapidly forward and possibly puncture or tear delicate internal organs. Since, the drop in resistance often occurs very suddenly, it can be very difficult to remove the force before injury occurs.

Medical personnel and patients are also placed at risk by the sharp tips of conventional trocars. Specifically, the sharp trocars make it very easy for medical personnel to inadvertently cut themselves or otherwise puncture their skin or gloves when using a conventional trocar. Not only are such accidental wounds painful, but they can also transfer the blood of the patient to the injured medical personnel or vice versa. With the increasingly widespread threat of HIV, the well-publicized AIDs virus, and other communicable diseases, the danger of accidental blood exchanges provides a clear danger to anyone involved with a conventional trocar. This is especially true when medical personnel are injured in a surgical setting since the patient's blood will likely be present when the accidental wound occurs. An accidental wound to a medical worker could, therefore, easily result in accidental blood exchanges between the injured party and the patient.

In addition to the serious risks detailed above, conventional trocars cause medical personnel many other problems. For instance, in many surgical procedures involving trocars, the body cavity is inflated with a nontoxic gas before the trocar is employed to create a working "pocket" or volume within the patient and to prevent the trocar from penetrating internal organs during insertion. For example, in an appendectomy, a patient's abdomen is first inflated with gas through a veress needle. The obturator is then used to place cannulas in various locations about the inflated abdomen for performing the procedure. One such cannula would typically be used to pass a small camera and light into the body cavity so a surgeon could view the operating area within the patient. Other cannulas would be used to pass surgical instruments into the cavity and remove tissue such as the appendix from the patient.

It is very important to maintain the abdomen of the patient in an inflated state throughout the procedure. To this end, conventional cannulas are often provided with sealing flap valves or the like which prevent gas from escaping from the patient's abdomen after the obturator is withdrawn. However, these sealing flap valves do not prevent gas leakage when a surgical instrument having a diameter which is smaller than the diameter of the cannula is employed. Instead, gas can easily pass through the gap between the inner wall of the cannula and the outer surface of the surgical instrument and deflate the work area. To prevent deflation of this type from occurring, physicians have often been required to utilize only those instruments whose dimensions closely match those of the cannula. This requirement inherently limits the surgeon's freedom of choice in selecting instruments for a procedure. Thus, while a certain instrument might be preferred by a physician, the physician might nonetheless be forced to use a less preferred (and possibly less effective) tool to perform a procedure to avoid deflating a body cavity.

Another problem conventional trocars present lies in the ease with which conventional cannulas can be inadvertently withdrawn from the working channel. Conventional cannulas typically include a smooth outer wall designed to facilitate insertion of the device through a body wall. The smooth surface of the cannula insures that the tissue surrounding the incision does not suffer excessive trauma when the cannula is passed through the body wall. Unfortunately, it also insures that the cannula can be withdrawn from the incision as smoothly and easily as it was inserted. This lack of resistance to withdrawal can easily result in the inadvertent withdrawal or removal of the cannula when an obturator or other surgical instrument is withdrawn. Inadvertent removals can create multiple problems, including deflation of the body cavity, splattering of body fluids, loss of time, and unnecessary trauma to the body tissue surrounding the working channel from the resulting multiple removals and insertions of the cannula.

OBJECTS OF THE INVENTION

It is, therefore, a general object of the present invention to provide an improved trocar for use in surgical procedures which protects both patients and medical personnel from injury. More specifically, it is an object of the invention to provide an improved trocar which will help prevent the inadvertent penetration of a patient's internal organs during insertion. It is a related object to provide an obturator whose sharp tip can only be exposed when the obturator is attached to a cannula.

It is another object of the present invention to provide a trocar assembly which does not limit a surgeon's choice of surgical instruments to those instruments having a specific diameter. It is a related object to provide a trocar assembly which can be used with surgical instruments of different diameters without deflating a body cavity and without replacing the trocar cannula, which was used for insertion, with a cannula of a different size.

It is yet another object of the invention to provide a trocar assembly which can be easily inserted into a body wall but which cannot be inadvertently withdrawn from the patient.

SUMMARY OF THE INVENTION

The present invention accomplishes these objectives and overcomes the drawbacks of the prior art by providing a trocar for use in surgical procedures which includes a cannula for maintaining a sealed working channel in a body wall and an obturator which protects patients and medical personnel from harm. In addition, the present invention provides a cannula converter for use with the trocar cannula which enables surgeons to use surgical instruments having smaller diameters than the trocar cannula without deflating a body cavity. Finally, the invention also provides a site stabilizer for use with the trocar which prevents the inadvertent withdrawal of the cannula from the patient's body wall during a surgical procedure.

As previously mentioned, the present invention provides an obturator which protects patients and medical personnel from harm. More specifically, the present invention provides an obturator which includes a shaft having a side wall defining a substantially hollow interior with substantially open, proximal and distal ends. The shaft includes an interior wall which runs within its hollow interior from one open end to the other such that the interior wall and the side wall combine to define multiple open-ended chambers. One end of the shaft is formed into a piercing tip to enable the obturator to penetrate a body wall. A handle is attached to the end of the shaft opposite the piercing tip.

In order to protect patients and medical personnel from injury, the obturator is further provided with safety shield members which are slidably disposed within the open-ended chambers of the shaft. These safety shield members extend the length of the shaft from the piercing tip into the handle chamber where they abut a spring. This spring biases the safety shield members into an extended position wherein the safety shield members surround the cutting edges of the piercing tip. Thus, when the obturator is pressed against a body wall, the safety shield members will compress the spring as they retract into the shaft. When the obturator penetrates the wall, the safety members will quickly move forward under the force of the spring to again cover the tip and protect the patient from harm.

Optionally, the obturator is further provided with a unique locking mechanism for controlling the translation of the safety shield members. This locking mechanism prevents the safety shield members from leaving the extended position when the obturator is disengaged from the cannula. In other words, the safety shield members can only be retracted when the obturator is attached to a cannula. When the obturator is disengaged from the cannula, the locking mechanism will insure that the safety shield members cover the piercing tip thereby preventing inadvertent injuries. Once the obturator engages a cannula, the locking mechanism will permit the members to retract. However, the locking mechanism will only permit the safety shield members to retract once. Consequently, after the safety shield members return to the extended position, they will be unable to retract unless the obturator is detached, and re-attached to a cannula to restart the procedure. Thus, the locking mechanism prevents the safety shield members from inadvertently retracting after penetrating a body cavity and thereby helps prevent inadvertent penetration of internal organs.

In accordance with another aspect of the invention, a cannula converter is provided which permits surgical instruments having a diameter which is smaller than the diameter of the included cannula to be used without deflating an inflated body cavity and without replacing the cannula, which was used for insertion, with a cannula having a smaller interior diameter. More specifically, the cannula converter includes a housing having a first portion and a second portion. The first and second portions of the housing each define an opening adapted to receive surgical instruments. The openings of the first and second portions communicate through a channel which permits surgical instruments to pass through the converter. The housing includes a seal for sealably engaging these surgical instruments. In addition, the converter is provided with an attachment assembly for attaching the housing to the trocar cannula such that surgical instruments can be passed through the converter and the trocar cannula for performing surgical procedures. In an optional embodiments the housing of the converter is further provided with a lip or rim for sealably engaging the cannula to help prevent deflation of the body cavity.

In accordance with yet another aspect of the invention, the trocar is also provided with a site stabilizer for preventing an attached trocar cannula from being inadvertently withdrawn from a body wall. The site stabilizer includes a stem which defines a channel for receiving the trocar cannula and which includes external threads for engaging the body wall of a patient. A head having a top portion and a bottom portion is connected to the stem. Both the top and the bottom portions of the head define an opening which is aligned with the channel defined by the stem for receiving the trocar cannula. The bottom portion of the head includes a camming structure. A handle which is slidably disposed at least partially within the head operatively engages the camming structure. A gripping device disposed adjacent the handle is actuated between a release position for receiving and releasing the trocar cannula and a grip position for securing and gripping the trocar cannula as the handle moves along the ramp structure. In an optional embodiment, the site stabilizer is further provided with a seal disposed within the head and positioned for receiving the cannula to help prevent deflation of the body cavity and to provide drag on the cannula during insertion.

It will be appreciated that any of the above-described components (i.e., the obturator, cannula, cannula converter or site stabilizer) can be used apart from the other components without departing from the invention. However, the trocar assembly, namely the obturator, cannula, cannula converter and site stabilizer, can also be used as a kit to overcome the above described problems associated with conventional trocars.

These and other features and advantages of the invention will be more readily apparent upon reading the following description of the preferred embodiment of the invention and upon reference to the accompanying drawings.

BRIEF DESCRIPTION OF THE DRAWINGS

FIG. 1 is a left, front perspective view of a trocar constructed in accordance with the teachings of the present invention;

FIG. 2 is a front side view thereof;

FIG. 11 is a fragmentary, front side view of the trocar with its safety shield members retracted;

FIG. 12 is a partial cross-sectional view of the trocar handle taken along lines 12—12 of FIG. 6 illustrating the locking mechanism in the released position;

FIG. 13 is a cross-sectional view taken along lines 13—13 of FIG. 12;

FIG. 14 is a cross-sectional view similar to FIG. 12 but illustrating the locking mechanism in the locked position;

FIG. 15 is a cross-sectional view similar to FIG. 12 but illustrating the locking mechanism in a second locked position.

FIG. 16 is a left, front perspective view of a cannula converter constructed in accordance with the teachings of the present invention;

FIG. 17 is a left, front perspective view of the cannula converter attached to the cannula;

FIG. 18 is a top plan view of the cannula converter;

FIG. 19 is a bottom plan view of the cannula converter;

FIG. 24 is a cross-sectional view of the cannula converter taken along lines 24—24 of FIG. 18;

FIG. 25 is an exploded view of the cannula converter illustrating the interaction of the seal housing and the attachment housing.

FIG. 27 is a left, front perspective view of the site stabilizer attached to the trocar;

FIG. 28 is a top plan view of the site stabilizer;

FIG. 29 is a bottom plan view of the site stabilizer;

FIG. 30 is a partial cross-sectional front side view of the site stabilizer;

FIG. 31 is a cross-sectional view of the site stabilizer taken along lines 31—31 of FIG. 30;

FIG. 32 is a cross-sectional view of the site stabilizer taken along lines 32—32 of FIG. 30;

FIG. 33 is an exploded view of the site stabilizer;

FIG. 34 is a partial cross-sectional view of the site stabilizer attached to the trocar illustrating the site stabilizer in the lock position;

FIG. 35 is a partial cross-sectional view of the site stabilizer attached to the trocar illustrating the site stabilizer in the release position;

DESCRIPTION OF THE PREFERRED EMBODIMENTS

Figure 8:
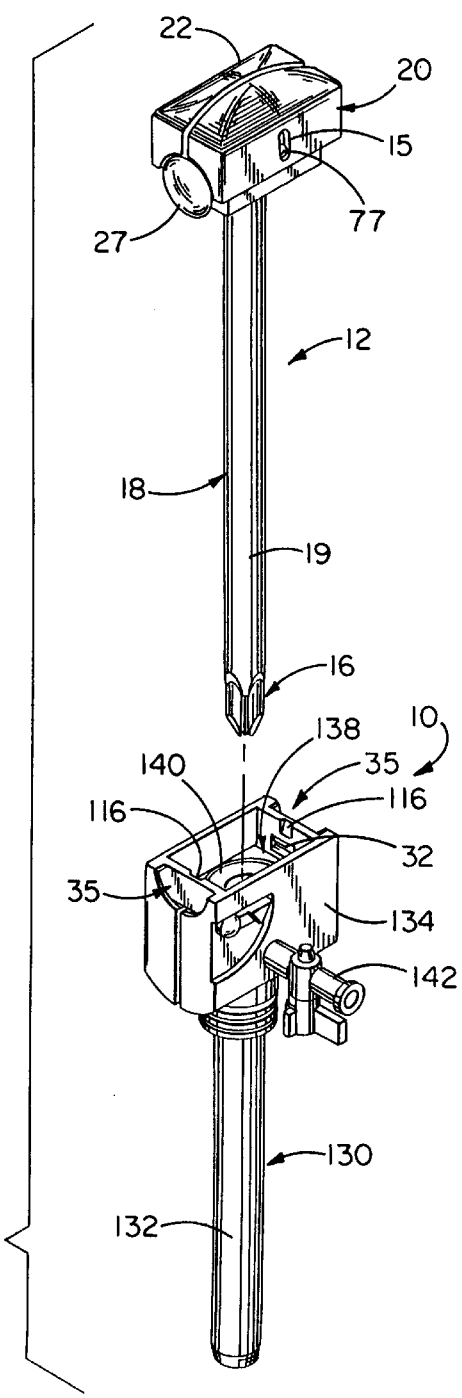
FIG. 8 is an exploded view thereof illustrating the obturator separated from the cannula.

A trocar 10 constructed in accordance with the teachings of the present invention is shown generally in FIG. 1. The trocar 10 is specifically constructed to create and maintain small working channels through a patient's body wall. To this end, the trocar 10 comprises two detachable components, namely, an obturator 12 and a cannula 130. As best seen in FIG. 8, the obturator 12 is the portion of the trocar 10 which actually creates the channel in the body wall. As explained in greater detail below, the obturator 12 is equipped with a sharp piercing tip 16 attached to a shaft 18 which terminates in a handle 20. The tip 16, shaft 18, and handle 20 combine to facilitate the insertion of the trocar 10 into a patient. The cannula 130 is the component of the trocar 10 which maintains the working channel for insertion of surgical instruments and the like during a given procedure. As discussed below, the cannula 130 includes an open-ended tube 132 which communicates with a handle 134 to provide a channel for receiving surgical instruments.

During insertion into a patient, the obturator 12 is first inserted into the cannula 130 such that the trocar 10 forms a single assembly as illustrated in FIG. 2. When assembled in this manner, the piercing tip 16 of the obturator 12 extends slightly beyond the open-ended tube 132 of the cannula 130. The trocar 10 can then be inserted into a patient such that the obturator 12 and the attached cannula 130 pierce the body wall of the patient. After insertion, the obturator 12 can be removed from the cannula 130 and the cannula 130 can be left in position to maintain a working channel for passing surgical instruments and the like into and out of the patient.

As previously mentioned, the obturator 12 includes a handle 20 which enables a physician to comfortably grip and insert a trocar 10 including the obturator 12 into a patient. Although other sizes and shapes might also be appropriate, the handle 20 preferably has a rectangular shape which can be easily gripped by a surgeon. Even more preferably, the top 22 of the handle 20 is contoured to provide a smooth, curved surface without sharp edges or points as illustrated in FIGS. 1–6. This smooth, curved top 22 enables a physician or surgeon to insert a trocar 10 employing the obturator 12 by applying force to the obturator handle 20 with the palm of their hand without discomfort.

As best seen in FIG. 8, the obturator handle 20 is preferably constructed to matingly engage the cannula handle 134. The obturator handle 20 and the cannula handle 134 thus combine to form a single handpiece 14 when the trocar 10 is assembled in a single assembly as illustrated in FIG. 2. This handpiece 14 is preferably sized to be comfortably gripped by a physician. To this end, the bottom 136 of the cannula handle 134 preferably has a smooth curved shape as illustrated in FIGS. 3–5 and 7. The smooth curved shape of the bottom 136 of the cannula handle 134 provides a comfortable surface for the physician's fingers during insertion of the trocar 10. The combination of the curved top 22 of the obturator handle 20 and the curved bottom 136 of the cannula handle 134 results in a handpiece 14 which a surgeon can comfortably hold and use with a single hand. Although the above described handpiece construction is preferred, it will be appreciated by those skilled in the art that handpieces having other shapes, sizes and configurations can also be employed without departing from the invention.

As illustrated in FIG. 12, the trocar 10 is preferably provided with an attachment assembly 24 for removably attaching the obturator handle 20 to the cannula handle 134. The attachment assembly 24 insures that the trocar 10 remains assembled as a single unit when inserted through a body wall. As illustrated in FIG. 15, the preferred attachment assembly 24 comprises two oppositely disposed pivotable buttons 27, 29 including tabbed arms 26, 28. The pivotable buttons 27, 29 and the tabbed arms 26, 28 are connected such that they pivot as a single unit. The pivotable buttons 27, 29 are pivotally mounted upon posts 25, 31 contained within a handle chamber 21 defined by the obturator handle 20. The buttons 27, 29 are pivotable between two extreme positions, a lock position wherein the tabbed arms 26, 28 are disposed at their most outward position for engaging notches 30, 32 in the cannula handle 134, and a release position wherein the tabbed arms 26, 28 are disposed at their most inward position free of the notches 30, 32. A spring 34 disposed adjacent to the tabbed arms 26, 28 biases the buttons 27, 29 into the lock position. Thus, when the trocar 10 is assembled as a single unit, the tabbed arms 26, 28 engage the notches 30, 32 and prevent the obturator 12 from inadvertently separating from the cannula 130. However, as illustrated in FIGS. 2, 4, 8 and 9 the buttons 27, 29 are positioned outside the assembled handpiece 14 within recesses 33, 35 in the exterior of the obturator handle 20 and cannula handle 134, respectively. Consequently, a user can overcome the biasing force of the button spring 34 by applying an inwardly directed force to the buttons 27, 29 and thus releasing the tabbed arms 26, 28 from the notches 30, 32 to separate the obturator 12 from the cannula 64.

In order to assist the attachment of the obturator 12 and the cannula 130, the cannula handle 134 is further provided with a pair of oppositely disposed lead-in ramps 116. As illustrated in FIG. 15, these lead-in ramps 116 provide smooth, inclined surfaces which encourage the tabbed arms 26, 28 of the pivotable buttons 27, 29 of the attachment assembly 24 to pass into the cannula handle 134 where they engage notches 30, 32, respectively.

Figure 10:
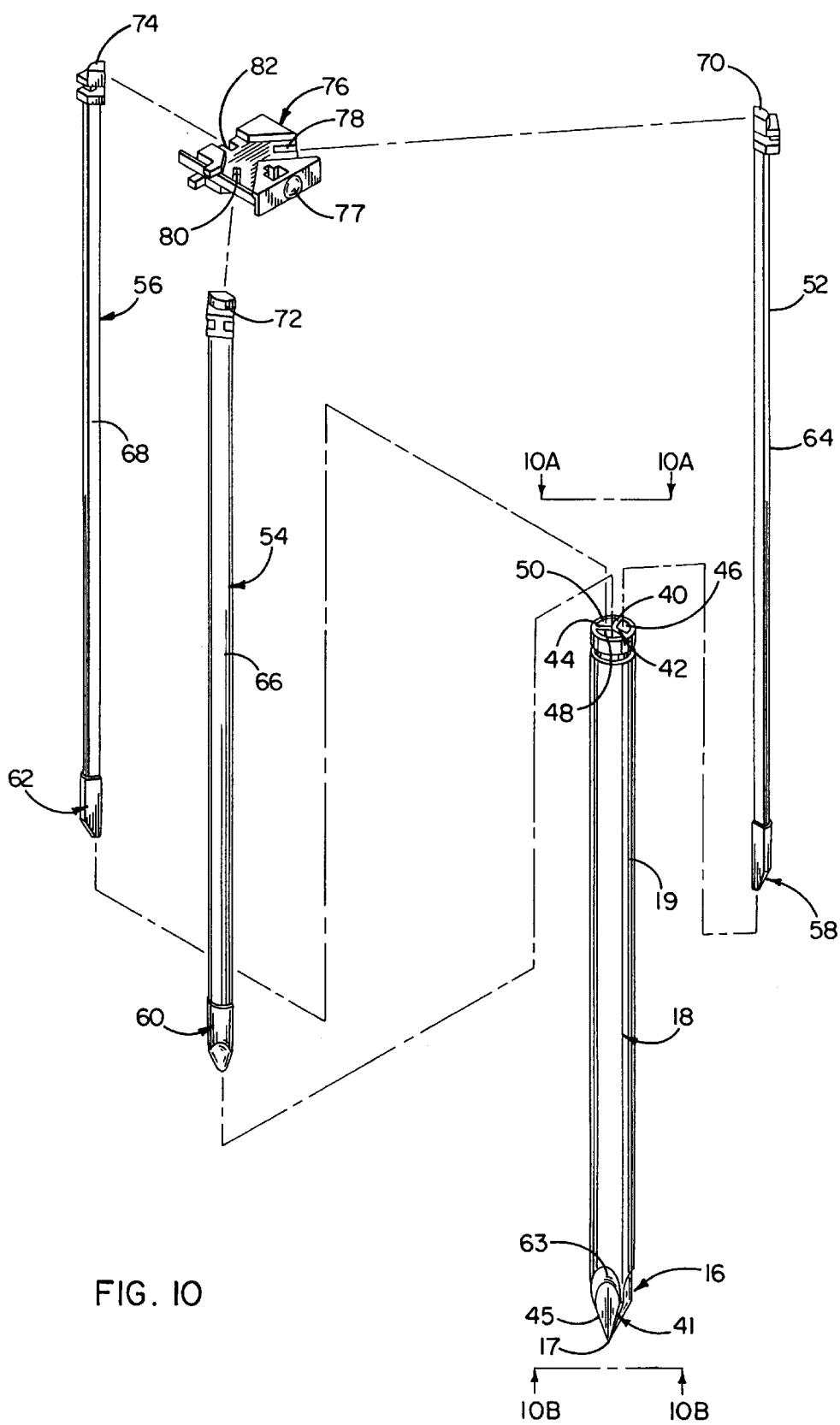
FIG. 10 is an exploded view of the safety shield members and obturator shaft illustrating the construction of the safety shield members.
Figure 10A:
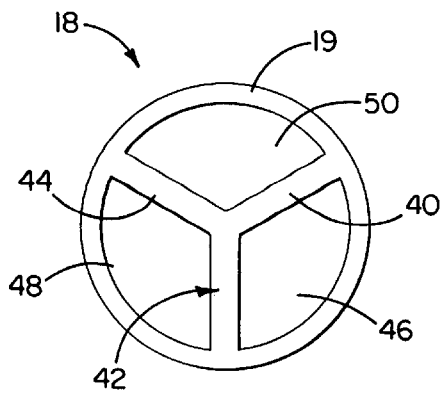
FIG. 10A is a top plan view of the shaft of the obturator taken along lines 10A—10A of FIG. 10.

In accordance with an aspect of the invention, the obturator 12 is provided with a shaft 18 for penetrating the body wall of a patient. As illustrated in FIGS. 10 and 10A, the shaft 18 preferably includes a cylindrical side wall 19 which defines a substantially hollow interior. Further, as illustrated in FIG. 10A, the shaft 18 is preferably provided with three interior walls 40, 42, 44 which divide the substantially hollow interior of the shaft 18 into three separate chambers 46, 48, 50. Both the walls 40, 42, 44 and the chambers 46, 48, 50 preferably extend the length of the shaft 18 from the proximal to the distal end. In addition, the opposite ends of the shaft 18 are open. Consequently, the chambers 46, 48, 50 are open-ended and, thus, provide passages completely through the shaft's interior. Since the proximal end of the open-ended shaft 18 is mounted within the handle chamber 21 as illustrated in FIG. 12, the chambers 46, 48, 50 defined by the side wall 19 and the interior walls 40, 42, 44 of the shaft 18 communicate with the interior of the handle chamber 21.

Figure 7:
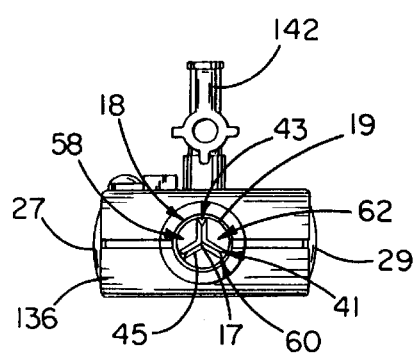
FIG. 7 is a bottom plan view thereof.
Figure 10B:
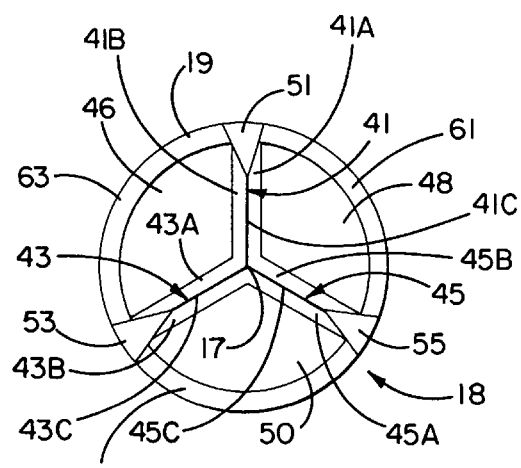
FIG. 10B is a bottom plan view of the shaft of the obturator taken along lines 10B—10B of FIG. 10.
Figure 10C:
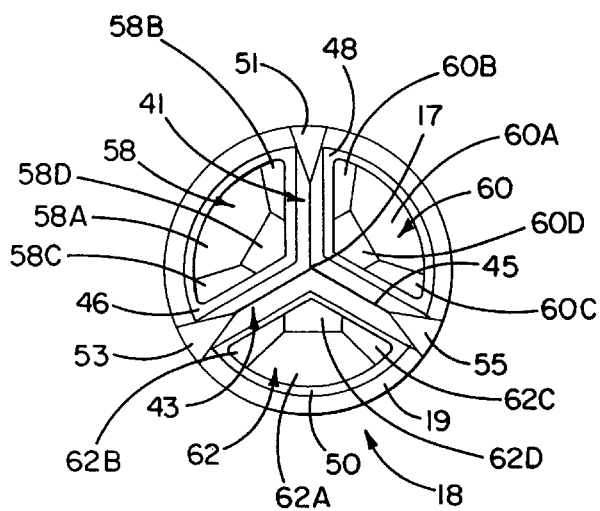
FIG. 10C is a bottom plan view similar to FIG. 10B but illustrating the safety shield members disposed in the shaft of the obturator.
Figure 10D:
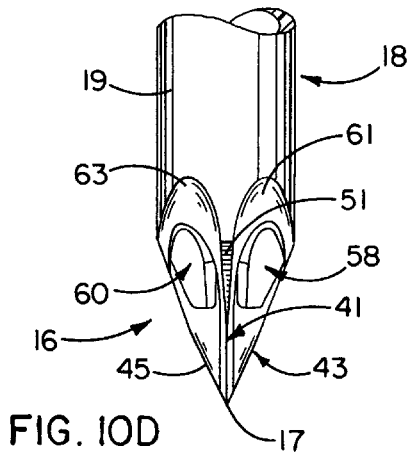
FIG. 10D is a partial, enlarged front side view of the piercing tip of the obturator illustrating the safety shield members in the retracted position.

As illustrated in FIG. 10, the end of the obturator shaft 18 opposite the obturator handle 20 is provided with a sharp piercing tip 16. This piercing tip 16 is preferably formed by sharpening the side 19 and interior walls 40, 42, 44 of the shaft 18 into a piercing point 17. Thus, in the preferred embodiment, the piercing tip 16 is integrally formed with the obturator shaft 18. In addition, since the piercing tip 16 is preferably formed by sharpening the side wall 19 and the interior walls 40, 42, 44 of the shaft 18, the preferred piercing tip 16 comprises three angularly positioned blades 41, 43, 45 configured in a substantially pyramidal shape as illustrated in FIGS. 7 and 10B. As best seen in FIG. 10B, each of these blades 41, 43, 45 includes a first end and a second end. The first ends of the blades 41, 43, 45 are joined to form the piercing point 17 and the second ends of the blades 41, 43, 45 engage the side wall 19 of the shaft 18. Further, to facilitate penetration of the body wall each blade 41, 43, 45 includes two oppositely angled side portions 41A, 41B, 43A, 43B, 45A, 45B which intersect to form sharp cutting edges 41C, 43C, 45C. The oppositely angled side portions 41A, 41B, 43A, 43B, 45A, 45B and the cutting edges 41C, 43C, 45C, are thus located between the first and second ends of the blades 41, 43, 45. As illustrated in FIGS. 10B, 10C and 10D, the blades 41, 43, 45 are positioned such that each pair of adjacent blades define an opening therebetween which communicates with one of the open-ended chambers 46, 48, 50.

It will, of course, be appreciated by those skilled in the art that although the preferred embodiment employs three interior walls 40, 42, 44 defining three chambers 46, 48, 50, other amounts of interior walls (i.e. 1, 2, 4, etc.) could also be employed without departing from the invention. Similarly, although the preferred embodiment employs a piercing tip 16 formed by sharpening the shaft's side 19 and interior walls 40, 42, 44 into a point 17, separate piercing tips affixed to the shaft 18 could be substituted without departing from the invention. Also, although the piercing tip 16 has been described as pyramidal in shape, other shapes could also be employed. Piercing tips having other shapes and configurations might be required, for example, if other than three interior walls and three interior chambers are employed. Finally, although the obturator shaft 18 has been illustrated as having a substantially circular cross-section it will be appreciated that shafts having cross-section of other shapes such as triangular, oval, hexagonal, etc. might likewise be appropriate. However, it will be appreciated by those skilled in the art that the use of shafts having non-circular cross-sections and configurations may require similar adjustments to the shapes and configuration of other components of the trocar 10 and, potentially, to other surgical instruments for use with the trocar 10.

In accordance with another aspect of the invention, the obturator 12 is provided with retractable safety shield members 52, 54, 56 slidably disposed within the open-ended chambers 46, 48, 50 defined by the interior walls 40, 42, 44 of the shaft 18. As illustrated in FIG. 10, these safety shield members 52, 54, 56 each include a tip 58, 60, 62, a shaft 64, 66, 68, and a tabbed end 70, 72, 74, respectively. The tabbed end 70, 72, 74 of each member 52, 54, 56 is preferably received by an attachment block 76 which binds the safety shield members 52, 54, 56 together such that the shield members move simultaneously. To this end, the attachment block 76 is provided with receiving slots 78, 80, 82, each of which receive a tabbed end 70, 72, 74 of a member 52, 54, 56. Preferably, the tabbed ends 70, 72, 74 slide into the retaining slots 78, 80, 82. However, alternate assembly methods employing adhesives, mechanical fasteners such as screws, or other techniques could also be used to permanently fasten the safety shield members 52, 54, 56 to the attachment block 76 without departing from the invention.

Figure 9:
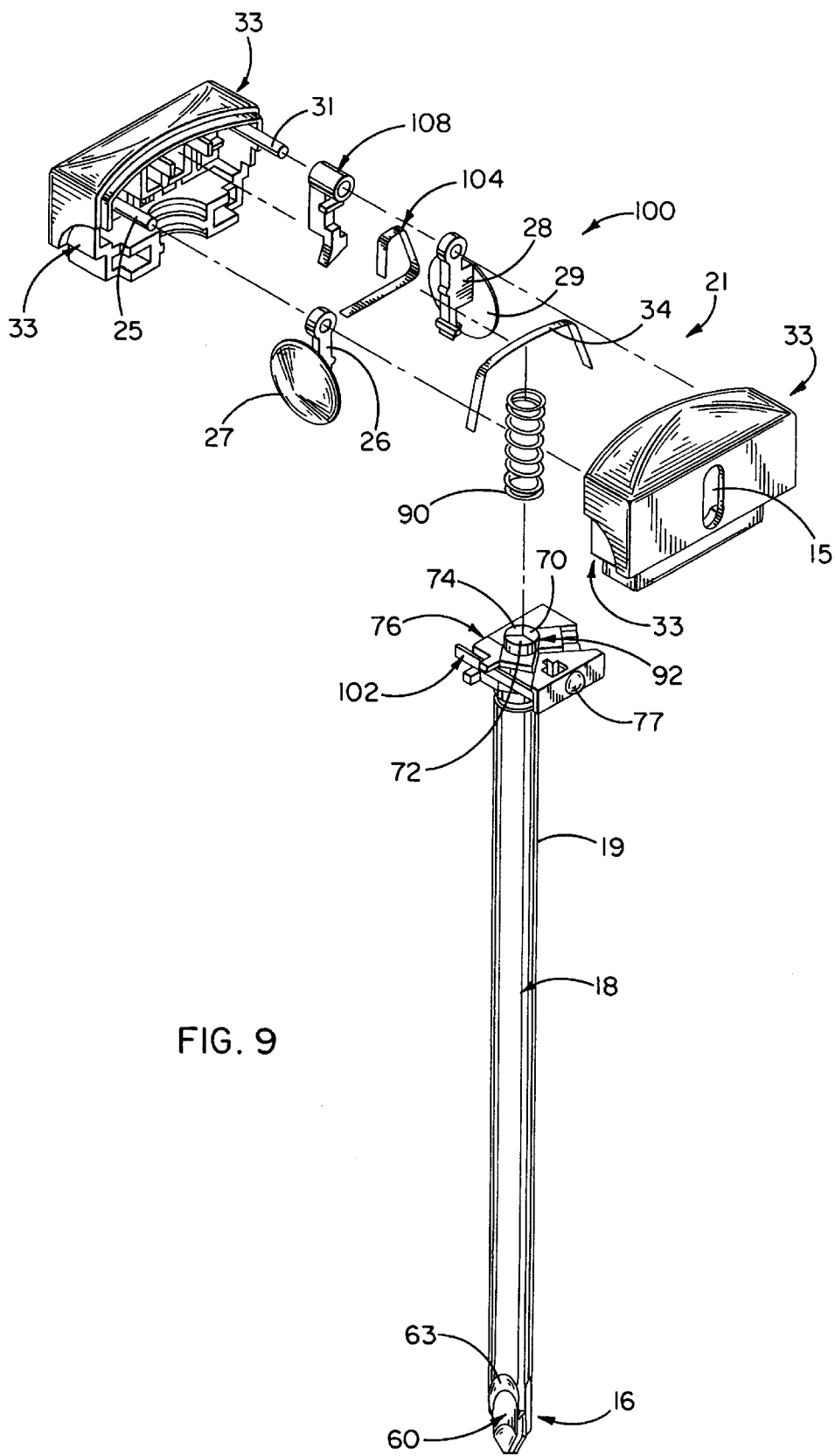
FIG. 9 is an exploded view of the obturator illustrating the construction of the obturator handle and the locking mechanism.

After the safety shield members 52, 54, 56 are secured to the attachment block 76, the members 52, 54, 56 are inserted into the chambers 46, 48, 50 of the obturator shaft 18 as illustrated in FIGS. 9 and 10C. In accordance with an important aspect of the invention, the individual shafts 64, 66, 68 of the safety shield members 52, 54, 56, which are preferably all substantially equal in length, are longer than the obturator shaft 18 itself. Consequently, even though the attachment block prevents the safety shield members 52, 54, 56 from passing completely into the shaft's chambers 46, 48, 50, the tips 58, 60, 62 of the members extend beyond the point 17 of the piercing tip 16 of the obturator 12. Thus, the safety shield members 52, 54, 56 combine to cover the piercing tip 16 and prevent the tip 16 from inadvertently cutting, piercing, or otherwise injuring an individual.

As illustrated in FIGS. 10B–10C, the individual blades 41, 43, 45 of the piercing tip 16 are blunted into triangular lands 51, 53, 55 near the outer wall 19 of the shaft 18. These lands 51, 53, 55 are preferably free of sharp edges. As best seen in FIG. 10C, the blunting of the blades 41, 43, 45 into lands 51, 53, 55, respectively, insures that the sharp, cutting surfaces of blades 41, 43, 45 do not extend beyond the safety shield members 52, 54, 56 when the members 52, 54, 56 are in the extended position. In other words, the blunting of the outer portions of the blades 41, 43, 45 insures that the sharp cutting edges 41C, 43C, 45C of these blades 41, 43, 45 are no longer than the corresponding sides of the tips 58, 60, 62 of the safety shield members 52, 54, 56 (i.e., from the piercing point 17 to the individual triangular lands 51, 53, 55).

As previously mentioned, the chambers 46, 48, 50 of the obturator shaft 18 communicate with the handle chamber 21. Thus, when the safety shield members 52, 54, 56 are inserted into the chambers 46, 48, 50, the attachment block 76 is disposed within the handle chamber 21. As illustrated in FIG. 9, when assembled with the attachment block 76 the tabbed ends 70, 72, 74 of the shield members 52, 54, 56 combine to form a circular gripping structure 92. This circular gripping structure 92, like the attachment block 76 is disposed within the handle chamber 21.

In order to control the movement of the slidably disposed safety shield members 52, 54, 56, the obturator 10 is further provided with a shield spring 90 as shown in FIG. 9. The shield spring 90 surrounds and grips the circular gripping structure 92 formed by the tabbed ends 70, 72, 74 of the shield members 52, 54, 56. Further, the shield spring 90 is disposed within the handle chamber 21 between the attachment block 76 and the interior of the obturator handle's top 22. As illustrated in FIGS. 11 and 12, the top 22 of the obturator handle 20 is provided with inwardly directed projections 94 which fix the position of the spring 90.

The shield spring 90 biases the safety shield members 52, 54, 56 distally towards the extended position wherein the shield members combine to cover the piercing tip 16. Thus, in order to move the safety shield members 52, 54, 56 into the retracted position illustrated in FIGS. 10D and 11, one must exert a force sufficient to overcome the biasing force of the shield spring 90 upon the shield members. Since the shield members 52, 54, 56 compress the spring 90 as they move towards the retracted position, the shield spring 90 will cause the shield members 52, 54, 56 to quickly move distally into the extended position to once again cover the piercing tip 16 as soon as this overcoming force is removed.

For example, when using the trocar 10 a physician will grip the assembled handpiece 14 and press the tips 58, 60, 62 of the safety shield members 52, 54, 56 against the body of the patient. When the physician exerts sufficient force to overcome the biasing force of the shield spring 90, the shield spring 90 will compress and the safety shield members 52, 54, 56 will retract into the obturator shaft 18 as illustrated in FIGS. 10D and 11. The retraction of the safety shield members 52, 54, 56 exposes the piercing point 17 and the sharpened blades 41, 43, 45 of the piercing tip 16 which, consequently, contact the patient's flesh. The piercing tip 16 then pierces the patient's body wall and, with continued pressure from the physician, passes completely into the patient's body.

It will be appreciated by those skilled in the art that the patient's body wall provides significant resistance to this penetration. Thus, in order to create an incision with the trocar 10, the physician must apply a similarly significant amount of force. It will also be appreciated by those skilled in the art that the resistance of the body wall will suddenly decrease by a substantial amount when the piercing tip 16 passes through the wall. Since the physician will likely be applying a significant amount of force to the trocar 10 at the instant the resistant drops, the sharp piercing tip 16 can potentially rush forward and injure the patient's internal organs. In order to avoid any such injury, it is imperative that the safety shield members 52, 54, 56 quickly return to the extended position to cover the piercing tip 16.

Figure 3:
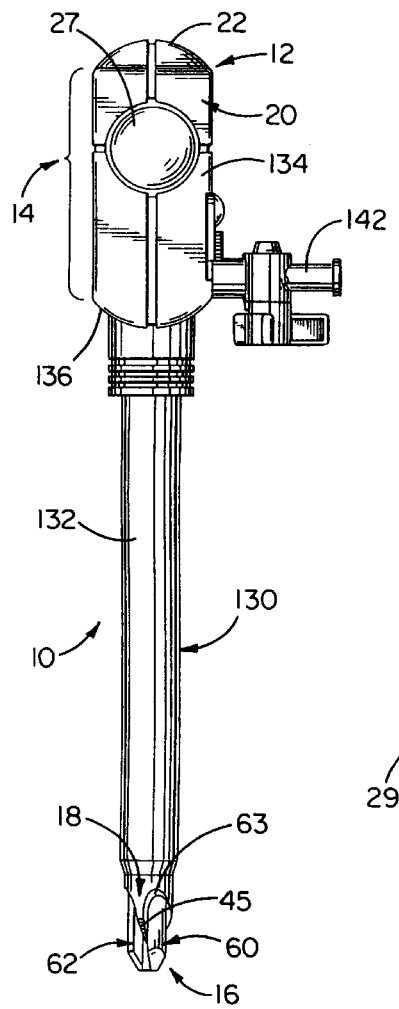
FIG. 3 is a left side view thereof.

As shown in FIGS. 2, 3 and 10D, the tips 58, 60, 62 of the safety shield members 52, 54, 56 are beveled preferably to each include at least one surface which is inclined at the same angle as the blades 41, 43, 45 of the piercing tip 16 such that the tips 58, 60, 62 and the blades align when the safety shield members 52, 54, 56 are in the retracted position as illustrated in FIGS. 10D and 11. In this position, the tips 58, 60, 62 of the safety shield members 52, 54, 56 form the sides of the pyramidal piercing tip 16 thereby creating a smooth piercing structure for pushing the flesh surrounding the incision aside and enabling the obturator shaft 18 and cannula tube 132 to easily pass into the patient without unnecessarily traumatizing the surrounding flesh.

To this end, each of the tips 58, 60, 62 of the safety shield members 52, 54, 56 include a central beveled portion 58A, 60A, 62A, two side portions 58B, 58C, 60B, 60C, 62B, 62C disposed on opposite sides of the central beveled portion 58A, 60A, 62A, and a blunted tip portion 58D, 60D, 62D as shown in FIG. 10C. The central beveled portions 58A, 60A, 62A each provide a large, smooth surface for pushing a patient's tissue aside with minimal trauma when the trocar 10 is inserted through a body wall. The oppositely disposed side portions 58B, 58C, 60B, 60C, 62B, 62C, align with the oppositely angled side portions 41A, 41B, 43A, 43B, 45A, 45B of the obturator shaft's blades 41, 43, 45 in the retracted position to prevent the patient's tissue from entering the open-ended chambers 46, 48, 50 during insertion. Finally, the blunted tip portions 58D, 60D, 62D provide a flat surface which will not easily cut or puncture tissue or internal organs to enhance the protective function of the safety shield members 52, 54, 56 during use. This construction of the tips 58, 60, 62 of the safety shield members 52, 54, 56 minimizes the amount of travel required of the safety shield members 52, 54, 56 from the extended to the retracted positions and vice versa. More specifically, the beveled construction of the 58, 60, 62 tips insures that the blades 41, 43, 45 are exposed for cutting and penetrating a body wall after only a short proximal movement of the safety shield members 52, 54, 56. This short travel distance from the extended position to the retracted position likewise insures that the safety shield members only travel a similarly short distance from the retracted to the extended position thereby minimizing the deployment time of the safety shield members 52, 54, 56 and reducing the risk of injury to internal organs during insertion of the trocar 10.

As illustrated in FIGS. 10B and 10D, portions 61, 63, 65 of the side wall 19 of the obturator shaft 18 are preferably beveled at substantially the same angle as the tips 58, 60, 62 of the safety shield members 52, 54, 56. Thus, when the safety shield members 52, 54, 56 are in the retracted position, these beveled portions 61, 63, 65 of the side wall 19 align with the beveled surfaces of the tips 58, 60, 62 of the shield members 52, 54, 56 to provide a smooth transition between the piercing tip 16 and the obturator shaft 18 thereby minimizing trauma to the patient's flesh during insertion. Preferably, the beveled portions 61, 63, 65 of the obturator shaft 18 are formed when the side wall 19 and inner walls 40, 42, 44 are sharpened to form the piercing tip 16.

As previously mentioned, the shield spring 90 causes the shield members 52, 54, 56 to deploy as soon as the force causing their retraction is removed. Thus, as soon as the sharp tip 17 and blades 41, 43, 45 of the piercing tip 16 pass through the patient's body wall, the beveled tips 58, 60, 62 of the safety shield members 52, 54, 56 will encounter less resistance and begin to return to their extended position. Moreover, the pyramidal shape of the obturator tip 16 insures that the patient's flesh is penetrated from the center outward. In other words, the piercing point 17 of the piercing tip 16 will first penetrate the body wall followed by the blades 41, 43, 45 and shield members in ever widening circles until the obturator shaft 18 and, preferably, the attached cannula 130 pass into the body cavity. Since the safety shield members 52, 54, 56 are mounted within the obturator shaft 18, the members will penetrate the body wall a short time before the shaft 18 and cannula tube 132. Consequently, the safety shield members 52, 54, 56 will begin to return to the extended position before the trocar 10 begins to move into the patient's body cavity thereby insuring that the piercing tip 16 is covered before injury to internal organs or other structures can occur.

It will be appreciated by those skilled in the art that the shield spring 90 must be chosen such that the spring 90 compresses and the safety shield members 52, 54, 56 retract before the patient's flesh is bruised, damaged or torn by the tips 58, 60, 62 of the shield members 52, 54, 56. On the other hand, the spring 90 should not be too easily compressed or inadvertent exposure of the piercing tip 16 could occur. Springs which generate spring forces between 0.3 lbs. and 1.6 lbs. should compress before any damage is done to the patient's tissue and yet require sufficient force to avoid inadvertent piercing tip exposures. Consequently, springs which generate spring forces between 0.3 lbs. and 1.6 lbs. are preferred in this role.

It should be noted, however, that trocars having different diameters will displace different amounts of tissue during penetration. Specifically, trocars having large diameters will displace more tissue than trocars having small diameters. As a result, trocars having larger diameters will require springs 90 which generate more force than trocars with small diameters. Thus, in the most preferred embodiments, a trocar 10 having a 5 mm diameter will employ a spring 90 which generates spring forces of approximately 0.3 lbs. when the shield members are fully extended and spring forces of approximately 1.0 lbs. when the shield members are fully retracted, and a trocar 10 having a diameter of 10 mm, 11 mm or 12 mm will employ springs 90 which generate spring forces of approximately 1.0 lbs. when the shield members are fully extended and spring forces of approximately 1.5 lbs. when the shield members are fully retracted. It will be appreciated that all of these preferred spring forces fall within the general preferred range of 0.3 lbs and 1.6 lbs. noted above.

In order to provide the physician with information concerning the position of the safety shield members 52, 54, 56, the trocar 10 is further provided with an indicator 77. As illustrated in FIG. 9, the indicator 77 preferably comprises a projection which is integrally formed with the attachment block 76 for movement therewith. This indicator 77 is received by an opening 15 in the obturator handle 20. Consequently, as illustrated in FIG. 2, the position of the indicator 77 can be easily viewed by a surgeon or physician employing the device 10. As illustrated in FIG. 2, when the safety shield members 52, 54, 56 are in their extended position (i.e. their distal or forwardmost position), the attachment block 76 and, thus, the indicator 77 are similarly in their forwardmost or distal positions. When, however, the safety shield members 52, 54, 56 are retracted as in FIGS. 10D and 11, the attachment block 76 and its connected indicator 77 also move to their proximal or rearward positions. By observing the relative position of the indicator 77 within the opening 15, the physician will thus be able to identify the state of deployment of the shield members 52, 54, 56.

The ability to identify the position of the shield members 52, 54, 56 can be important because, as explained in detail below, the safety shield members 52, 54, 56 can be locked in their extended position. When this occurs, the physician cannot cause the members 52, 54, 56 to retract regardless of the force the physician exerts on the trocar 10. If a physician were unable to easily determine the position of the safety shield members 52, 54, 56 the physician might exert excessive force in an attempt to force the shielded tip 16 through the patient's body wall. This could result in unnecessary trauma to the patient's flesh. Such trauma should not occur with the inventive trocar 10 because a physician will be able to see that the members 52, 54, 56 are not retracting before exerting excessive force.

In addition, as explained above, the safety shield members 52, 54, 56 should begin to return to the extended position before the cannula 130 enters the patient's body cavity. The physician should be able to discern this distal or forward motion of the shield members 52, 54, 56 by viewing the indicator and, thus, be forewarned that total penetration is imminent. Consequently, the physician will have an opportunity to decrease the applied pressure before the trocar 10 totally pierces the body wall to avoid forcing the blunted tips 58, 60, 62 of the safety shield members 52, 54, 56 against internal organs.

Figure 4:
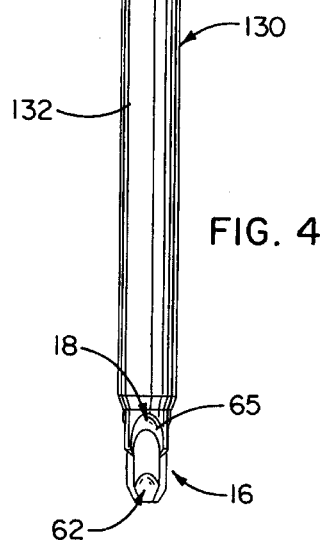
FIG. 4 is a back side view thereof.
Figure 5:
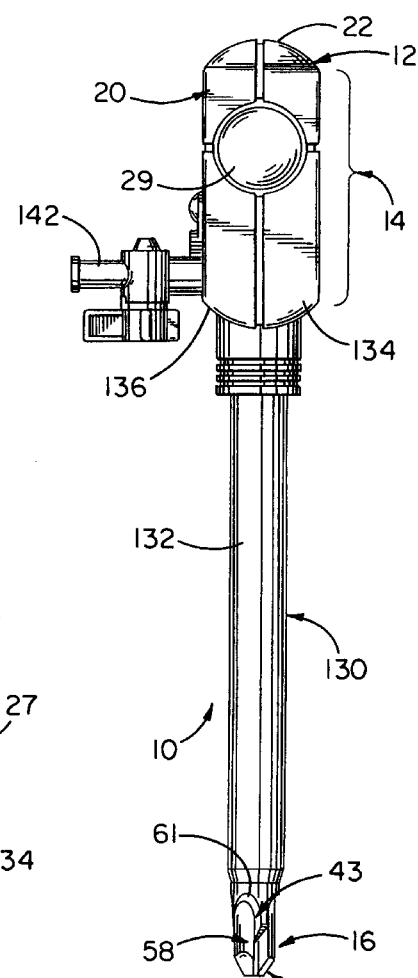
FIG. 5 is a right side view thereof.
Figure 6:
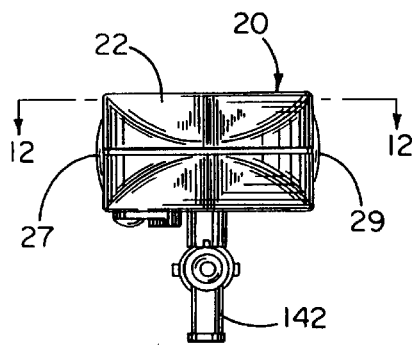
FIG. 6 is a top plan view thereof.

As illustrated in FIG. 4, the back side of the obturator handle 20 preferably is not provided with an indicator. Accordingly, although the obturator handle 20 and cannula handle 134 can be assembled into a single handpiece in either of two orientations (i.e. in the position illustrated in FIG. 1 or with the obturator 12 rotated 180° with respect to the cannula 130), it is preferable that the physician orient the obturator and cannula handles 20, 134 such that the indicator 77 is most visible to the physician during use. Nonetheless, it will be appreciated by those skilled in the art that a second indicator could be placed on the back side of the obturator handle 20 such that an indicator appears on both sides of the handle 20 to avoid these concerns with orientation without departing from the claimed invention.

In accordance with another aspect of the invention, the obturator 12 is preferably provided with a locking mechanism 100 for controlling the translation of the safety shield members 52, 54, 56. As illustrated in FIGS. 9 and 12, the locking mechanism 100, which is disposed within the obturator handle chamber 21, includes a first spring 102 attached to the attachment block 76 for movement therewith, a second spring 104 operatively engaging the first spring 102, a stop 106 attached to the interior of the obturator handle 20 and having a stop projection 106A, and a translatable arm 108 operatively engaging the second spring 104.

As best seen in FIG. 13, the first spring 102 has an L-shape with a first leg 101 of the "L" engaging the attachment block 76 adjacent the indicator 77 and the other leg 103 disposed substantially perpendicularly to the first leg 101. Although the entire first spring 102 is carried by and travels with the attachment block 76, the second leg 103 of the first spring 102 also translates between a lock position (illustrated in FIG. 14) and a release position (illustrated in FIG. 12) in a direction transverse to the movement of the attachment block 76. To this end, the second leg 103 of the first spring 102 is biased to the left in FIG. 12A. When in the lock position, the second leg 103 of the first spring 102 prevents the safety shield members 52, 54, 56 from retracting into the handle chamber 21 by abutting the stop 106.

Figure 12A:
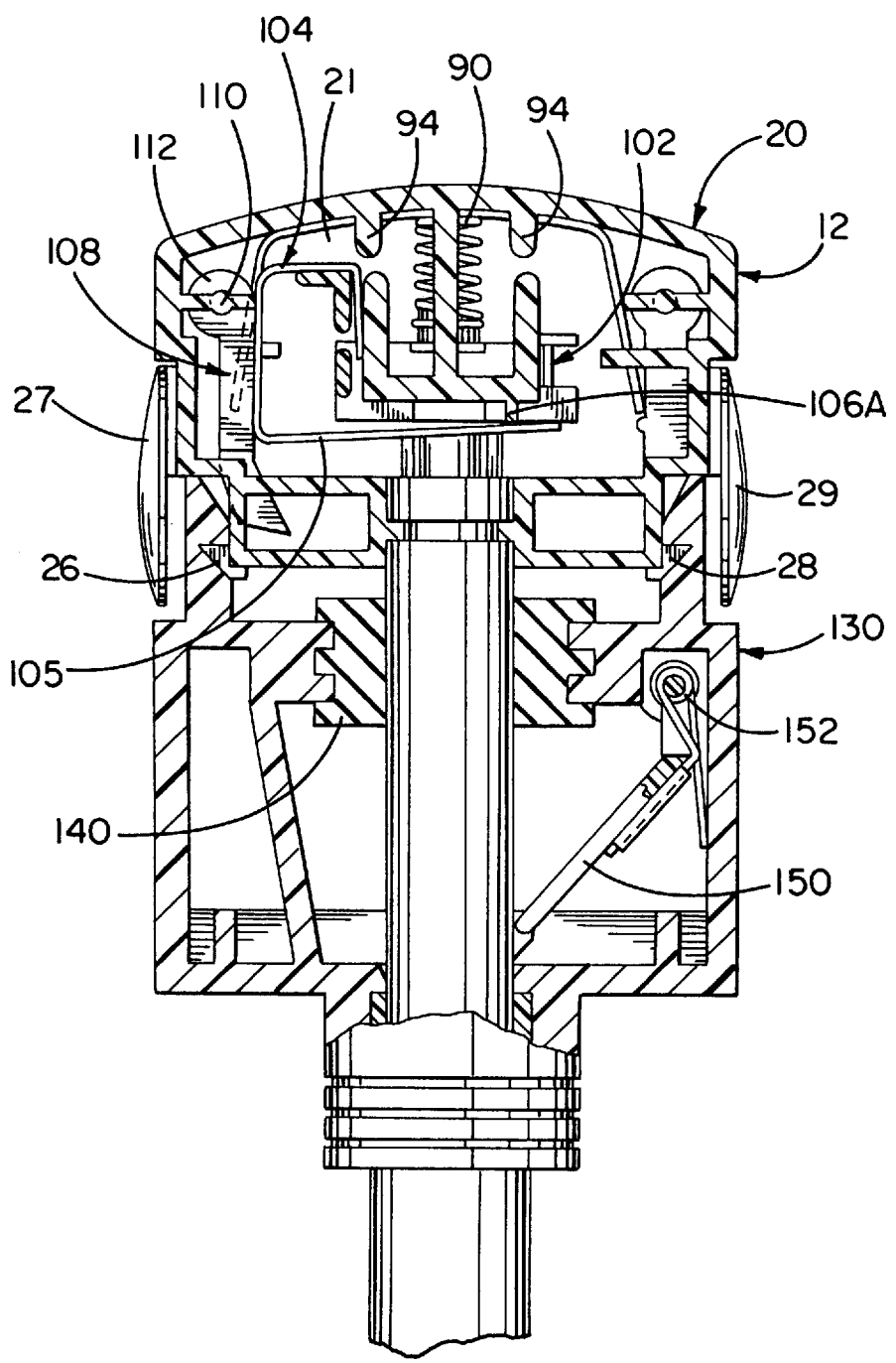
FIG. 12A is a cross-sectional view similar to FIG. 12, but illustrating the locking mechanism when the safety shield members are retracted.

As shown in FIG. 12, this stop 106 is a projection affixed to the interior of the obturator handle 20. When the first spring 102 is in the lock position, its second leg 103 is below and abuts the stop 106 thereby preventing the attachment block 76 from moving rearward or distally as illustrated in FIG. 14. Consequently, the safety shield members 52, 54, 56 cannot retract into the shaft 18 to expose the piercing tip 16. On the other hand, when the first spring 102 is displaced into the release position illustrated in FIGS. 12 and 13, the attachment block 76 and the safety shield members 52, 54, 56 can freely retract because the spring 102 will pass around (as shown in FIG. 12A), rather than abut, the stop 106 (as shown in FIG. 14).

In order to control the movement of the first spring 102 between the lock and release positions, the locking mechanism 100 is further provided with a second spring 104. As shown in FIG. 12, the second spring 104 is disposed in a plane which is substantially perpendicular to the second leg 103 of the first spring 102. Unlike the first spring 102, however, the second spring 104 is not secured to the attachment block 76. Instead, the second spring 104 is secured within the obturator handle 20. Further, the second spring 104 is biased for movement in two directions, namely, towards the stop projection 106A disposed upon stop 106 (i.e. upwards in FIG. 12) and away from the first spring 102 (i.e. to the left in FIG. 12).

As best seen in FIG. 15, the translatable arm 108 is pivotally mounted upon a post 110 adjacent the second spring 104. The translatable arm 108 includes a head 112 which receives the post 110 and an elongated leg 114. As illustrated in FIG. 15, the elongated leg 114 passes through an opening in the obturator handle 20 to engage the cannula handle 134 when the trocar 10 is assembled into a single unit. Since the second spring 104 is biased away from the first spring 102, the second spring 104 exerts an outward force upon the translatable arm 108 which moves the arm 108 to the left position illustrated in FIG. 15 whenever the obturator 12 is separated from the cannula 130.

When the biasing force of the second spring 104 moves the translatable arm to the left (i.e. whenever the obturator handle 20 is separated from the cannula handle 134), the leg 105 of the second spring 104 likewise moves to the left. Before the obturator handle 20 and the cannula handle 134 are separated, the first spring 102 can be in one of two positions, the lock position or the release position. If the safety shield members 52, 54, 56 have been previously retracted, the leg 103 of the first spring 102 will be in the lock position (i.e. below the stop 106 and above the second spring 104) as illustrated in FIG. 14. If so, the leftward movement of the leg 105 of the second spring 104 will not effect the position of the first spring 102. However, the leg 105 of the second spring 104 will slide past the first spring 102 and snap upward into contact with the stop projection 106A of stop 106 such that the leg 105 of the second spring 104 is behind the side 107 of the first spring 102 as illustrated in FIG. 15. If, on the other hand, the safety shield members 52, 54, 56 have not been previously retracted, the leg 103 of the first spring 102 will initially be disposed in the release position illustrated in FIGS. 12 and 13 (i.e. with the leg 105 of the second spring 104 already abutting both the side 107 of the leg 103 and the stop projection 106A of the stop 106). Thus, when the obturator and cannula handles 20, 134 are detached, both the first and second springs 102, 104 move to the left simultaneously since they are biased in that direction. Consequently, the locking mechanism 100 will move from the position illustrated in FIG. 12 into the position illustrated in FIG. 15.

Thus, it will be appreciated that regardless of the initial position of the first spring 102 (i.e. lock or release), the separation of the obturator handle 20 from the cannula handle 134 will always cause the locking mechanism 100 to move into the second locked position illustrated in FIG. 15. Consequently, the locking mechanism 100 prevents the safety shield members 52, 54, 56 from retracting whenever the obturator 12 and cannula 130 are separated. However, when the obturator handle 20 is re-attached to the cannula handle 134, the elongated leg 114 of the translatable arm 108 contacts the cannula handle 134 and, thus, moves the translatable arm 108 and the adjacent second spring 104 back to the right and into the position illustrated in FIG. 12. Since the second spring 104 abuts the side 107 of the leg 103 of the first spring 102, the leg 105 forces the leg 103 to translate into its release position. Thus, the locking mechanism 100 minimizes the risk of injury by insuring that the piercing tip 16 can only be exposed when the trocar 10 is completely assembled for use in a surgical procedure.

In use, the physician or surgeon first inserts the obturator 12 into the cannula 130. Prior to connecting the obturator handle 20 and the cannula handle 134, the locking mechanism 100 is in the position illustrated in FIG. 15. In other words, the translatable arm 108 and the leg 105 of the second spring 104 are in their leftmost position and the leg 103 of the first spring arm 102 is in the lock position. When the obturator handle 20 and cannula handle 134 are first assembled into a single handpiece 14, the translatable arm 108, the leg 105 of the second spring 104 and the leg 103 of the first spring 102 move into the position illustrated in FIG. 12 as explained above. Thus, the leg 103 of the first spring arm 102 moves to the release position such that the safety shield members 52, 54, 56 are free to move into the retracted position illustrated in FIG. 11.

The physician then places the shielded piercing tip 16 against the patient's body wall and begins to apply force to the trocar 10. When the force applied by the physician exceeds the biasing force of shield spring 90, the safety shield members 52, 54, 56 retract into the shaft 18 exposing the piercing tip 16 of the obturator 12. As illustrated in FIG. 12A, the movement of the safety shield members 52, 54, 56 causes the first spring 102 and the leg 103 to translate with the attachment block 76 past the stop 106, thereby disengaging from the leg 105 of the second spring 104. As the piercing tip 16 passes into the patient's body cavity and the safety shield members 52, 54, 56 return distally towards the extended position, the first spring 102 and the leg 103 move forward contacting the leg 105 of the second spring 104.

As the first spring 102 moves forward under the force of shield spring 90, the leg 103 of the first spring 102 displaces the leg 105 of the second spring 104 away from the stop projection 106A of the stop 106. As illustrated in FIG. 14, the relative positions of the first and second springs 102, 104 are thus reversed. The leg 103 of first spring 102 now abuts the side of the leg 105 of the second spring 104 rather than vice versa. Accordingly, the leg 105 of the second spring 104 can no longer prevent the leg 103 of the first spring 102 from moving into the lock position. Consequently, the leg 103 of the first spring 102 moves into the lock position adjacent stop projection 106A but under the largest portion of stop 106 thereby locking the safety shield members 52, 54, 56 in the extended position and preventing further retraction.

If the physician wishes to re-arm the trocar 10 so that the shield members 52, 54, 56 can once again retract, the physician must repeat the above described process. In other words, the physician must first detach the obturator handle 20 from the cannula handle 134 such that the locking mechanism 100 translates into the position illustrated in FIG. 15. Then, the physician must re-attach the handles 20, 134 to return the locking mechanism 100 to the position shown in FIG. 12 wherein the leg 103 of the first spring 102 is once again free of the stop 106.

Other than the features of the attachment assembly 24 and locking mechanism 100 explained above (i.e. notches 30, 32, and lead-in ramps 116), the cannula 130 includes the standard cannula features known in the art. Specifically, the cannula 130 is provided with an open-ended tube 132 which communicates with a cannula handle 134 for receiving surgical instruments and the like during a surgical procedure. In addition, as illustrated in FIG. 8, the cannula handle 134 includes an opening 138 for receiving the surgical instruments which are passed through the interior of the handle 134 and the open-ended tube 132. In order to prevent the inert gas which is often used to inflate a patient's body cavity in a surgical procedure from escaping around inserted surgical instruments, the cannula opening 138 is provided with an annular seal 140. This seal 140 abuts the outer diameter of inserted instruments thereby minimizing the amount of gas leakage.

As illustrated in FIG. 12A, the cannula 130 is additionally provided with a spring loaded sealing flap 150 which prevents gas from escaping when the cannula 130 is not carrying an instrument or obturator 12 as is known in the art. This sealing flap 150, which is disposed within the cannula handle 134, is preferably biased into contact with the opening 138 by a torsion spring 152 such that the flap 150 blocks the opening 138 and prevents gas from leaking when the cannula tube 132 is empty.

Finally, as illustrated in FIG. 8, the cannula 130 is also provided with a valve 142 for inflating and deflating the body cavity. The operation and construction of the valve 142, like the other standard features of the cannula 130, is well known in the art and, thus, need not be described in detail here. Instead, it is sufficient to note that a tube carrying pressurized gas from an external gas source can be affixed to the valve 142 and the valve 142 can be opened and closed to permit a desired amount of gas to enter the body cavity for inflation. On the other hand, the valve 142 can be attached to a hose and opened to deflate the cavity and drain the gas into a container.

Some of the components of the trocar 10 such as the valve 142 are commercially available products. Since these components are well known in the art, there is no need to discuss specific techniques for manufacturing them here. Many of the other components such as the obturator handle 20, the safety shield members 52, 54, 56, the attachment block 76, the cannula tube 132, and the cannula handle 134 are preferably constructed from molded plastic using standard molding techniques which are well known in the art. Finally, the seals 140 and springs 90, 102, 104, 34, 152 mentioned above are all constructed using manufacturing techniques which are well known in the art. However, spring 90 is preferably made of 302 stainless steel and constructed to generate spring forces between 0.3 lbs. and 1.6 lbs; spring 102 is preferably made of 301 stainless steel and constructed to generate forces of approximately 1.3 lbs.; spring 104 is preferably made of 301 stainless steel and constructed to generate forces in an axial direction (i.e. co-axially with the shaft) of approximately 0.08 lbs.; spring 34 is preferably made of 301 stainless steel and constructed to generate spring forces of approximately 0.22 lbs.; and torsion spring 152 is preferable made of 302 stainless steel and constructed to generate spring torques between 0.12 in-lbs. when the flapper door is closed and 0.6 in-lbs when the flapper door is open. It will be appreciated, however, that although springs generating forces as noted above are preferred, springs exhibiting other force generating characteristics might likewise be appropriate.

The multi-chambered obturator shaft 18 and integrally formed piercing tip 16, can be constructed by first extruding aluminum through a die of an appropriate shape to form a multi-chambered tube. The extruded aluminum may then be cut into workpieces of any desired length. One end of the workpiece can then be sharpened to form a piercing tip. Specifically, the shaft 18 can be sharpened by grinding, planing or otherwise cutting the side 19 and inner walls 40, 42, 44 of the shaft 18. Referring to FIGS. 10A, 10B and 10D, a first cut would be made at an angle to the outer wall 19 thereby forming beveled portion 63 and opening 46. A second cut would be made at substantially the same angle to the outer wall 19 but oriented to form beveled portion 61 and opening 48. The combination of these first two cuts would create the sharp blade 41 between openings 48 and 46. A third and final cut would then be made on the side opposite that illustrated in FIG. 10D. This final cut would create beveled portion 65 and two sharp blades 43 and 45. Triangular lands 51, 53, and 55 could then be formed by grinding, milling or turning the blades 41, 43, and 45 until they have the appropriate lengths. The completed shaft 18 can then be assembled with the other described components of the obturator 12. As previously mentioned, the remainder of the trocar components can be manufactured with molding and tooling techniques which are well known to those skilled in the art.

A cannula converter 210 constructed in accordance with the teachings of the present invention is shown generally in FIG. 16. As illustrated in FIG. 17, the cannula converter 210 is constructed for use with the above described cannula 130. As mentioned above, the cannula 130 includes an annular seal 140 for surrounding the exterior of surgical instruments which have been inserted into the cannula 130. However, if a surgeon wishes to employ a surgical instrument having an exterior diameter smaller than the interior diameter of the cannula tube 132, a gap can exist between the annular seal 140 and the surgical tool. Such a gap can permit gas to escape from the patient's body cavity. The cannula converter 210 overcomes this problem by operatively decreasing the inner diameter of the cannula 130.

As illustrated in FIG. 25, the cannula converter 210 includes a housing having two interlocking components, namely, a seal housing or first housing component 211, and an attachment housing or second housing component 213. As shown in FIG. 16, the seal housing 211 includes a top portion 212 defining an opening 214 adapted for receiving surgical instruments. An annular seal 240 similar to the annular seal 140 contained in the cannula handle 134 is disposed within the opening 214. The annular seal 240 of the cannula converter 210 preferably has a smaller interior diameter 219 than the seal 140 of the cannula 130. Thus, the annular seal 240 of the cannula converter 210 can receive surgical instruments with smaller diameters than the annular seal 140 of the cannula 130 and still prevent gas from escaping from the inflated body cavity.

Preferably, the area of the top portion or side 212 surrounding the opening 214 is molded into a smooth concave depression 215 as illustrated in FIG. 18. This depression 215 acts as a lead-in and visual target for inserting surgical instruments. In addition, the depression 215 enables the surgeon to insert surgical instruments further into the body cavity than would otherwise be possible.

As shown in FIG. 19, the bottom portion or side 216 of the attachment housing or second housing component 213 also defines an opening 218. This opening 218 is aligned with the opening 214 of the seal housing 211 such that instruments passing through the top opening 214 can also pass directly through the bottom opening 218. Further, the bottom portion 216 of the attachment housing 213, like the top portion 212 of the seal housing 211, includes a concave depression 217 around the opening 218. However, the bottom opening 218 is not provided with a seal.

Figure 20:
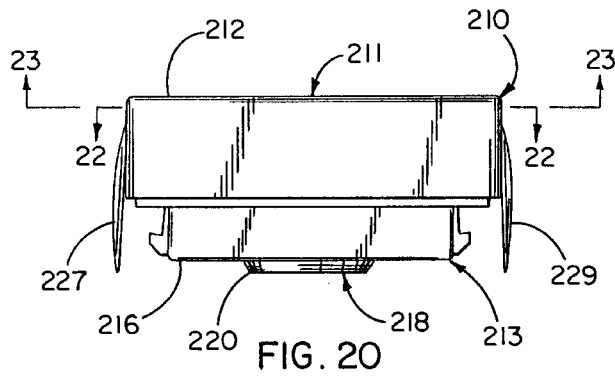
FIG. 20 is a front side view of the cannula converter.
Figure 21:
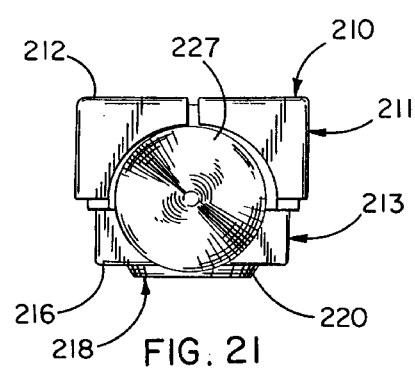
FIG. 21 is a left side view of the cannula converter.

Moreover, as illustrated in FIG. 20, the opening 218 in the bottom side 216 of the attachment housing 213 is surrounded by an outwardly projecting rim or lip 220. When the cannula converter 210 is connected to a cannula 130, this outwardly projecting rim 220 firmly abuts the annular seal 140 of the cannula handle 134 to form a seal which inhibits gas leakage between the cannula 130 and the converter 210.

Figure 23:
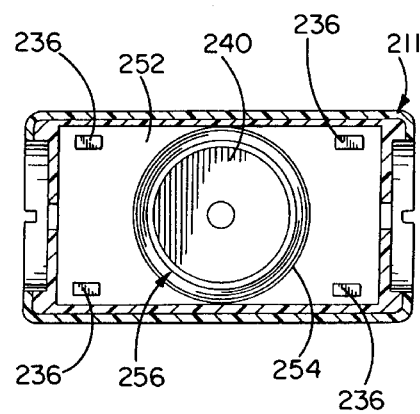
FIG. 23 is a cross-sectional view of the cannula converter taken along lines 23—23 of FIG. 20.

As illustrated in FIG. 24, the seal housing 211 and the attachment housing 213 combine to form a sealed channel 250 for passing surgical instruments between the top and bottom openings 214, 218. As shown in FIGS. 23 and 24, the bottom portion 252 of the seal housing 211 includes an inwardly projecting wall 254 defining an open-ended channel 256. This open-ended channel 256 communicates with the opening 214 in the top portion 212 of the seal housing 211. However, the interior diameter of the open-ended channel 256 is slightly larger than the interior diameter of the opening 214. Consequently, the annular seal 240, whose outer diameter preferably closely matches the inner diameter of the open-ended channel 256, preferably rests adjacent the opening 214 against an annular ledge 223. This annular ledge 223 prevents the seal 240 from passing through the opening 214.

Figure 22:
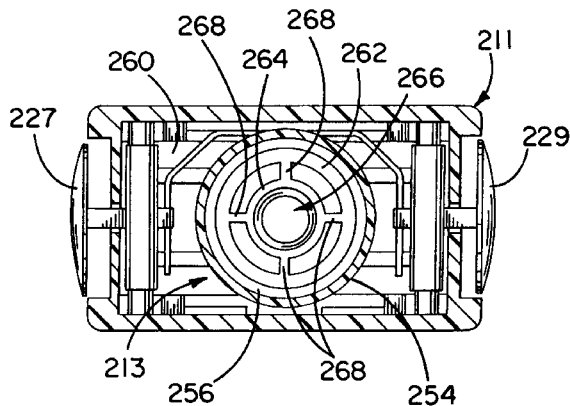
FIG. 22 is a cross-sectional view of the cannula converter taken along lines 22—22 of FIG. 20.

As illustrated in FIG. 22, the top portion 260 of the attachment housing 213 also includes an inwardly projecting wall 262. However, unlike the seal housing 211, the attachment housing 213 is also provided with a second inwardly directed wall 264. The second wall 264 is concentrically aligned with the first wall 262 and is preferably spaced from the first wall 262 by spacers 268. Further, the second wall 264 defines an open-ended channel 266 which communicates with the opening 218 in the bottom portion of the attachment housing 213. The outer diameter of the first wall 262 of the attachment housing 213 is slightly smaller than the inner diameter of the inwardly projecting wall 254 of the seal housing 211. Consequently, the walls 262, 264 of the attachment housing 213 are insertable into the inwardly projecting wall 254 of the seal housing 211 as illustrated in FIG. 24. Thus, when the seal and attachment housings 211, 213 are assembled, the inwardly projecting walls 262, 264 of the attachment housing 211 extend into the open-ended channel 256 of the seal housing 213 to form a single sealed channel 250 running between the openings 214, 218 of the seal and attachment housings 211, 213, respectively.

In the preferred embodiment, the inwardly projecting walls 262, 264 of the attachment housing 213 extend completely through the open-ended channel 256 of the seal housing 211 to compress the annular seal 240 firmly against the annular ledge 223 described above. The compression of the annular seal 240 prevents gas leakage from the sealed channel 250.

In order to attach the cannula converter 210 to the cannula 130, the cannula converter 210 is provided with an attachment device 224 which is very similar to the attachment device 24 described above in connection with the obturator 12. Thus, as illustrated in FIG. 25, the attachment device 24 includes two oppositely disposed pivotable buttons 227, 229 and a button spring 234. The pivotable buttons 227, 229 each include a tabbed arm 226, 228 and are disposed on opposite sides of the cannula converter 210 as illustrated in FIGS. 20, 21, 22 and 24. These tabbed arms 226, 228 engage the notches 30, 32 in the cannula handle 134 in the same manner as the tabbed arms 26, 28 of the pivotable buttons 27, 29 of the attachment device 24 employed by the obturator 12. Thus, the button spring 234 is positioned adjacent the tabbed arms 226, 228 and biases the arms outward as illustrated in FIG. 22. By exerting an inwardly directed force sufficient to overcome the biasing force of the button spring 234, the physician can disengage the arms 226, 228 from the notches 30, 32 and remove the converter 210 from the cannula 130.

However, whereas the pivotable buttons 27, 29 of the obturator 12 were pivotally mounted on posts 25, 31, the pivotable buttons 227, 229 of the cannula converter 210 include integrally attached posts 225, 231. Further, these posts 225, 231 are each pivotally seated upon a pair of carriages 237, 239, respectively. As illustrated in FIG. 25, these carriages 237, 239 include rounded seats 238 which permit the button posts 225, 231 to rotate. In order to insure these posts 225, 231 remain firmly seated during their rotations, the bottom 252 of the seal housing 211 is provided with four pads 236 as shown in FIG. 23. Each of these pads 236 is positioned directly above a rounded carriage seat 238. When the converter 210 is assembled, these pads 236 abut the posts 225, 231 of the buttons 227, 229 thereby permitting the posts 225, 231 to rotate upon the carriages 237, 239 while preventing them from becoming dislodged.

Most of the components of the cannula converter 210 are preferably constructed from plastic using molding techniques which are well known in the art. However, the button spring 234 is preferably constructed from 302 stainless steel using manufacturing techniques which are well known to those skilled in the art. Further, although the spring 234 preferably generates forces of approximately 0.7 lbs., springs of other strengths could also be used without departing from the invention.

Figure 26:
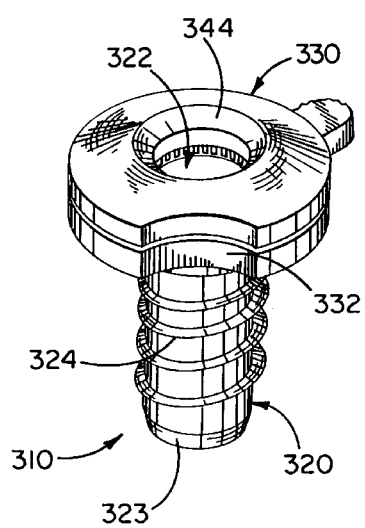
FIG. 26 is a front perspective view of a site stabilizer constructed in accordance with the teachings of the present invention.
Figure 36:
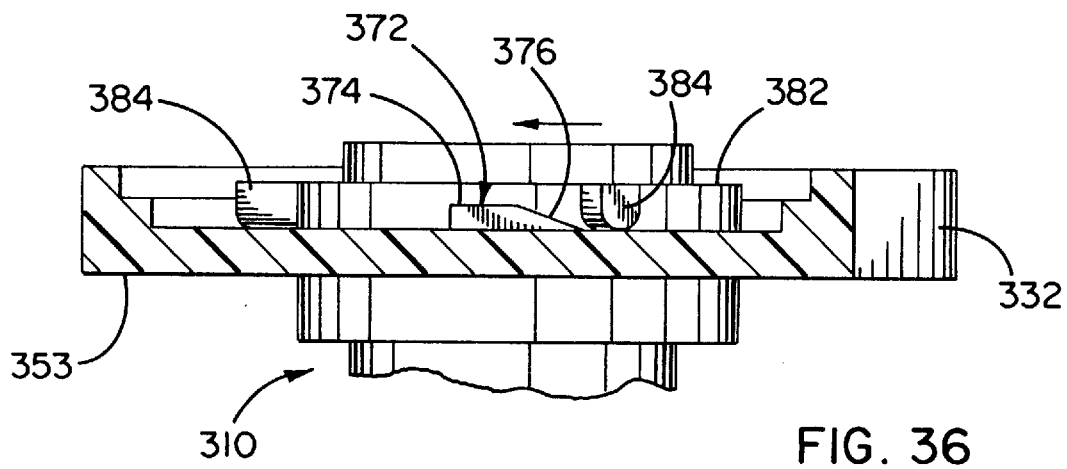
FIG. 36 is an enlarged, cross-sectional view of the site stabilizer handle interacting with the camming structure taken along lines 36—36 of FIG. 31 illustrating the handle in the release position.
Figure 37:
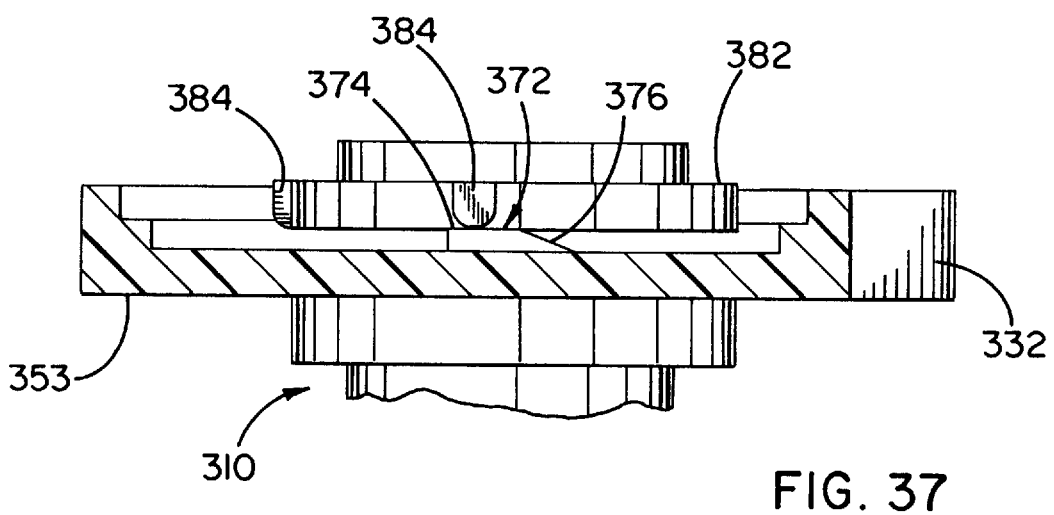
FIG. 37 is an enlarged, cross-sectional view similar to FIG. 36 but illustrating the handle in the lock position.

A site stabilizer 310 constructed in accordance with the teachings of the present invention is shown generally in FIG. 26. As previously mentioned, trocar cannulas such as the cannula 130 discussed above are often provided with a smooth exterior surface to facilitate insertion into a patient and to avoid excessive trauma to the flesh surrounding the incision. However, this ease of insertion typically also means that the cannula 130 can be inadvertently removed from the patient when withdrawing instruments such as the obturator 12. As illustrated in FIG. 27, the site stabilizer 310 overcomes these problems by providing a threaded exterior for the cannula 130 which can be used to grip the patient's flesh and prevent accidental withdrawals.

As illustrated in FIGS. 26 and 30, the site stabilizer 310 is provided with a stem 320 defining an open-ended channel 322 for receiving the cannula 130. In order to attach the cannula 130 to a patient's body wall, the stem 320 of the site stabilizer 310 includes external threads 324 which surround the cylindrical stem 320 and can be screwed into a patient's body wall. When threaded into a patient in this manner, the site stabilizer 310 can be withdrawn by reverse threading the threads 324 out of the incision. In order to facilitate the insertion of the stem 320 into the incision, the bottom of the stem 320 is tapered. This tapered portion 323 provides a smooth transition between the cannula and the site stabilizer as illustrated in FIG. 27.

As illustrated in FIG. 30, the site stabilizer 310 is further provided with a head 330. When the site stabilizer 310 is fully threaded into a body wall, the head 330 abuts the patient's skin to prevent the stabilizer 310 from passing completely into the body cavity. Preferably, the head 330 has a flattened shape which permits the cannula 130 to penetrate nearly as far into the patient as it would otherwise have reached. The broad, flattened shape of the preferred head 330 also provides a large surface for the physician to grip when threading the stabilizer into or out of the patient. To this end, the head 330 of the stabilizer 330 is further provided with a contoured finger notch 332 as shown in FIGS. 28 and 29. This finger notch 332 provides a secure resting point for the physician's thumb or other digit when gripping the stabilizer head 330 thereby avoiding the slipping problems that could be associated with a completely round head and providing a secure gripping surface for the physician when activating the handle 386 as described in detail below.

As illustrated in FIG. 33, the head 330 preferably comprises two parts, namely, a top portion 340 and a bottom portion 350. As shown in FIGS. 31 and 32, the top portion 340 and the bottom portion 350 of the head 330 each include an outer rim 343, 353. The top and bottom rims 343, 353, which project in opposite directions, are sealed together as illustrated in FIGS. 30 and 34 such that the flattened head defines an interior chamber.

As shown in FIG. 28, the top portion 340 of the head 330 defines an opening 342 which is concentrically aligned with the open-ended channel 322 defined by the stem 320. Thus, the cannula 130 can pass directly through the opening 342 and into the stem 322. Preferably, the area of the top portion 340 surrounding the opening 342 is molded into a smooth concave depression 344. This depression 344 acts as a lead-in ramp to guide the cannula 130 into the site stabilizer 310 during insertion. In addition, the depression 344 serves the same purpose as the flattened nature of the head 330 itself. Specifically, it enables the surgeon to insert the cannula 130 further into the body cavity than would otherwise be possible.

As shown in FIG. 33, the bottom portion 350 of the head 330 also defines an opening 352 which is concentrically aligned with the opening 342 of the top portion 340 and the open-ended channel 322 defined by the stem 320. Thus, when the site stabilizer 310 is attached to a cannula 130, the cannula 130 passes through both openings 342, 352 of the flattened head 330, and the open-ended channel 322.

In order to prevent gas from leaking from the patient's body cavity through the site stabilizer 310, the site stabilizer 310 is further provided with an annular sealing ring or O-ring seal 360. As illustrated in FIG. 33, this annular sealing ring 360 is disposed in an annular depression 354 in the bottom portion 350. Thus, when a cannula 130 is inserted through the openings 342, 352 of the head 330, the sealing ring 360 grips the cannula's exterior thereby limiting gas leakage through the open-ended channel 322. The O-ring seal 360 also provides drag on the cannula 130 to hold the position of the site stabilizer 310 when the trocar 10 is being inserted.

In order to secure the site stabilizer 310 to the cannula 130, the site stabilizer is further provided with a camming structure 370, a translatable handle 380, and a gripping device 390 all disposed at least partially within the interior of the head 330. As illustrated in FIG. 33, the camming structure 370 preferably comprises three upwardly projecting ramps 372 radially disposed around the opening 352 in the bottom portion 350 of the head 330. Each of these ramps 372 preferably includes an inclined portion 374 angling upwards from the bottom portion 350 of the head 330 and a flat portion 376 attached to the inclined portion 374. However, it will be appreciated by those skilled in the art that other ramp structures having other numbers of ramps or ramps without flattened portions 376 could likewise be employed.

The translatable handle 380 preferably includes a central hub 382 concentrically aligned with the openings 342, 352 and channel 322 and having a central opening 383 through which the cannula 130 passes, three radially projecting structures or projections 384 attached to the central hub 382 for operatively engaging the camming structure 370, and a manually engageable elongated arm 386. The elongated arm 386 of the translatable handle 380 extends through an opening 387 in the bottom rim 353 of the head 330 as illustrated in FIGS. 33, 34 and 35. Thus, the elongated arm 386 can be manually translated between a release position and a grip position.

In the release position illustrated in FIG. 31, the radially disposed projections 384 are each disposed upon the bottom portion 350 of the head 330 immediately adjacent an inclined portion 374 of a ramp 372 of the camming structure 370. However, as the elongated arm 386 is translated towards the grip position, the radially projecting structures 384 each engage an inclined portion 374 of a ramp 372 of the camming structure 370 and move upwards towards the flattened portions 376. This translation up the ramps 372 of the camming structure 370 elevates the central hub 382 of the translatable handle 380 with respect to the head 330 such that the hub 382 engages the gripping device 390.

As illustrated in FIG. 32, the gripping device 390 is preferably friction fit into a downwardly projecting, circular wall 345 attached to the interior of the top portion 340 of the head 330. Thus, the gripping device 390 is suspended directly above the central hub 382 of the translatable handle 380. Further, as illustrated in FIG. 33, the gripping device 390 preferably comprises an annular ring 392 including a plurality of radially spaced, inwardly directed projections 394 which translate between a first and a second position. In the first position, the inwardly directed projection are directed downward at a first angle, preferably at approximately a 45° angle from the annular rim 392. When the central hub 382 abuts the gripping device 390, it forces the inwardly directed projections 394 upwards from the first position illustrated in FIG. 35 into the second position illustrated in FIG. 34. This upward translation causes the projections 394 to extend further towards the center of the annular rim 392. Thus, the upward movement of the central hub 382 effectively decreases the inner diameter of the gripping device 390.

As shown in FIGS. 34 and 35, the cannula 130 passes through the center of the gripping device 390. Consequently, when the inner diameter of the gripping device 390 is effectively reduced by the upward movement of the inwardly directed projections 394, the gripping device 390 firmly grips the cannula 130 as shown in FIG. 34. Thus, the movement of the translatable handle 380 from the release position to the grip position forces the site stabilizer 310 to firmly grip the cannula 130. When the handle 384 is translated back to the release position, the projections 394 will return to their original position thereby releasing the cannula 130 from the site stabilizer 310 as shown in FIG. 35.

In order to control the movement of the translatable handle 380, the top portion 340 of the head 330 is provided with a camming structure preferably comprising downwardly extending ramps 347 as shown in FIG. 32. Preferably, these downwardly extending ramps 347 are disposed adjacent the ramps 372 of the bottom portion 350 of the head 330. The oppositely disposed ramps 347, 372 thus combine to define bounded channels for guiding the radially projecting structures 384 as they move between the release and lock positions as illustrated in FIG. 30.

Although other materials and construction techniques might likewise be appropriate, most of the components of the site stabilizer 310 are constructed from plastic using molding techniques which are well known in the art. However, the O-ring seal 360 is preferably constructed from silicon using common production techniques which are well known to those skilled in the art. Even more preferably, the silicon used to construct the O-ring seal 360 is the silicon sold under the product name "Baysilone" by Miles Inc. of Pittsburgh, Pa. 15205-9741.

Although the invention has been described in connection with certain embodiments, there is no intent to limit the invention to those embodiments. On the contrary, the intent is to cover all alternatives, modifications and equivalents included within the spirit and scope of the invention as defined by the appended claims.

What is claimed is:

1. A site stabilizer for preventing inadvertent withdrawal of a trocar cannula from a body wall comprising:

a stem defining a channel for receiving the trocar cannula and having external threads for engaging the body wall;

a head connected to the stem, the head having a top portion and a bottom portion, the top portion and bottom portion each defining an opening aligned with the channel of the stem for receiving the trocar cannula, the bottom portion including a camming structure;

a handle slidably disposed at least partially within the head and operatively engaging the camming structure; and a gripping device disposed adjacent the handle, the gripping device translating between a release position for receiving and releasing the trocar cannula and a grip position for securing and gripping the trocar cannula as the handle moves along the camming structure.

2. A site stabilizer as defined in claim 1 wherein the stem is cylindrical.

3. A site stabilizer as defined in claim 1 wherein the bottom portion of the head defines a recessed area aligned with the channel of the stem, the recessed area containing an O-ring seal.

4. A site stabilizer as defined in claim 1 wherein the top portion of the head includes a camming structure aligned with the camming structure of the bottom portion of the head to define bounded channels for guiding the handle.

5. A site stabilizer as defined in claim 1 wherein the camming structure comprises ramps radially disposed about the channel.

6. A site stabilizer as defined in claim 5 wherein the handle includes radially disposed projections for operatively engaging the radially disposed ramps of the camming structure.

7. A site stabilizer as defined in claim 1 wherein the gripping device further comprises an annular ring having a plurality of radially disposed inwardly directed projections, the inwardly directed projections being translatable from a first position wherein the projections are disposed at a first angle from the annular ring to define a first inner diameter for receiving the trocar cannula when the gripping device is in the release position and a second position wherein the projections are disposed at a second angle to define a second inner diameter which is smaller than the first inner diameter for gripping the trocar cannula when the gripping device is in the grip position.

* * * * *